United States Patent
Bayer

(10) Patent No.: US 9,617,332 B2
(45) Date of Patent: Apr. 11, 2017

(54) CONFORMATIONAL-SPECIFIC ANTIBODIES AGAINST A[β] OLIGOMERS

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventor: Thomas Bayer, Göttingen (DE)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

(*) Notice: Subject to any disclaimer, the term of this patent is extended or adjusted under 35 U.S.C. 154(b) by 0 days.

(21) Appl. No.: 14/399,639

(22) PCT Filed: May 8, 2013

(86) PCT No.: PCT/EP2013/059632
§ 371 (c)(1),
(2) Date: Nov. 7, 2014

(87) PCT Pub. No.: WO2013/167681
PCT Pub. Date: Nov. 14, 2013

(65) Prior Publication Data
US 2015/0118239 A1 Apr. 30, 2015

(30) Foreign Application Priority Data
May 10, 2012 (EP) .................................... 12167565

(51) Int. Cl.
C07K 16/18 (2006.01)
G01N 33/68 (2006.01)

(52) U.S. Cl.
CPC ......... C07K 16/18 (2013.01); G01N 33/6896 (2013.01); C07K 2317/33 (2013.01);
(Continued)

(58) Field of Classification Search
None
See application file for complete search history.

(56) References Cited

U.S. PATENT DOCUMENTS 4,816,567 A 3/1989 Cabilly et al.
7,763,249 B2 7/2010 Sugimura et al.

FOREIGN PATENT DOCUMENTS

EP 2 210 901 A1 7/2010
EP 2 246 427 A1 11/2010
(Continued)

OTHER PUBLICATIONS

Rudikoff et al. Proc Natl Acad Sci USA, 1982; 79(6):1979-1983.*
(Continued)

Primary Examiner — Jeffrey Stucker
Assistant Examiner — Aurora M Fontainhas
(74) Attorney, Agent, or Firm — Birch, Stewart, Kolasch & Birch, LLP

(57) ABSTRACT

The present disclosure relates to a conformational specific antibody molecule recognizing a conformational epitope of human trimeric or tetrameric Aβ oligomers, wherein said antibody molecule does not bind human monomeric Aβ 1-42 or human Ap 1-42 dimers; and pharmaceutical and diagnostic compositions comprising said antibody molecule as well as methods using same.

20 Claims, 14 Drawing Sheets

(52) U.S. Cl.
CPC .... *C07K 2317/34* (2013.01); *C07K 2317/565* (2013.01); *C07K 2317/76* (2013.01); *G01N 2500/02* (2013.01); *G01N 2500/10* (2013.01); *G01N 2800/2821* (2013.01)

(56) References Cited

FOREIGN PATENT DOCUMENTS

| WO | 2009065054 | * | 5/2009 | ............ G01N 33/53 |
|---|---|---|---|---|
| WO | WO 2009/056490 A1 | | 5/2009 | |
| WO | WO 2009/065054 A2 | | 5/2009 | |
| WO | WO 2011/151076 A2 | | 12/2011 | |

OTHER PUBLICATIONS

Paul, Fundamental Immunology, (textbook), 1993, pp. 292-295, under the heading "Fv Structure and Diversity in Three Dimensions".*
Citron, Alzheimer's disease: strategies for disease modification. Nat Rev Drug Discov. May 2010;9(5):387-98.*
Ahmed et al., "Structural conversion of neurotoxic amyloid-$\beta_{1-42}$ oligomers to fibrils", Nature Structural & Molecular Biology, vol. 17, No. 5, May 2010 (Published online Apr. 11, 2010), pp. 561-568.
Benilova et al., "The toxic Aβ oligomer and Alzheimer's disease: an emperor in need of clothes", Nature Neuroscience, vol. 15, No. 3 (Published online Jan. 29, 2012), Mar. 2012, pp. 349-357.
Billman-Jacobe, "Expression in bacteria other than *Escherichia coli*", Current Opinion in Biotechnology, vol. 7, 1996, pp. 500-504.
Bitter et al., "Expression and Secretion Vectors for Yeast", Methods in Enzymology, vol. 153, 1987, pp. 516-544.
Buchhave et al., "Cerebrospinal Fluid Levels of β-Amyloid 1-42, but Not of Tau, Are Fully Changed Already 5 to 10 Years Before the Onset of Alzheimer Dementia", Arch Gen Psychiatry, vol. 69, No. 1, Jan. 2012, pp. 98-106.
Casas et al., "Massive CA1/2 Neuronal Loss with Intraneuronal and N-Terminal Truncated Aβ$_{42}$ Accumulation in a Novel Alzheimer Transgenic Model", American Journal of Pathology, vol. 165, No. 4, Oct. 2004, pp. 1289-1300.
Chimon et al., "Evidence of fibril-like β-sheet structures in a neurotoxic amyloid intermediate of Alzheimer's β-amyloid", Natural Structural & Molecular Biology, vol. 14, No. 12, Dec. 2007 (Published online Dec. 2, 2007), pp. 1157-1164.
Coloma et al., "Novel vectors for the expression of antibody molecules using variable regions generated by polymerase chain reaction", Journal of Immunological Methods, vol. 152, 1992, pp. 89-104.
Fukumoto et al., "High-molecular-weight β-amyloid oligomers are elevated in cerebrospinal fluid of Alzheimer patients", The FASEB Journal, vol. 24, Aug. 2010, pp. 2716-2726.
Griffiths et al., "Production of Heterologous Proteins Using the Baculovirus/Insect Expression System", Methods in Molecular Biology, vol. 75, 1997, pp. 427-440.
Gurtu et al., "IRES Bicistronic Expression Vectors for Efficient Creation of Stable Mammalian Cell Lines", Biochemical and Biophysical Research Communications, vol. 229, Article No. 1, 1996, pp. 295-298.
Haass et al., "Soluble protein oligomers in neurodegeneration: lessons from the Alzheimer's amyloid β-peptide", Nature Reviews Molecular Cell Biology, vol. 8, Feb. 2007, pp. 101-112.
Hampel et al., "Biomarkers for Alzheimer's disease: academic, industry and regulatory perspectives", Nature Reviews Drug Discovery, vol. 9, Jul. 2010, pp. 560-574.
Haupt et al., "Structural Basis of β-Amyloid-Dependent Synaptic Dysfunctions", Angew Chem Int Ed, vol. 51, 2012, pp. 1576-1579.
Hockney, "Recent developments in heterologous protein production in *Escherichia coli*", Trends in Biotechnology, vol. 12, 1994, pp. 456-463.
International Preliminary Report on Patentability and the Written Opinion of the International Searching Authority(Forms PCT/IB/326, PCT/IB/373, and PCT/ISA/237), dated Nov. 20, 2014, for International Application No. PCT/EP2013/059632.
Jäger et al., "α-secretase mediated conversion of the amyloid precursor protein derived membrane stub C99 to C83 limits aβgeneration", Journal of Neurochemistry, vol. 111, 2009, pp. 1369-1382.
Jawhar et al., "Motor deficits, neuron loss, and reduced anxiety coinciding with axonal degeneration and intraneuronal Aβ aggregation in the 5XFAD mouse model of Alzheimer's disease", Neurobiology of Aging, vol. 33, 2012, Issue 1, Jan. 2012, pp. 196.e29-196.e40.
Kang et al., "The precursor of Alzheimer's disease amyloid A4 protein resembles a cell-surface receptor", Nature, vol. 325, Feb. 19, 1987, pp. 733-736.
Kayed et al., "Common Structure of Soluble Amyloid Oligomers Implies Common Mechanism of Pathogenesis", Science, vol. 300, Apr. 18, 2003, pp. 486-489.
Kim et al., "Development of Conformation-Specific Antibodies for Neutralization of β-Amyloid Oligomers", Neurobiology of Aging, vol. 25, Abstract P1-175, p. S145.
Klyubin et al., "Amyloid β Protein Dimer-Containing Human CSF Disrupts Synaptic Plasticity: Prevention by Systemic Passive Immunization", The Journal of Neuroscience, vol. 28, No. 16, Apr. 16, 2008, pp. 4231-4237.
Klyubin et al., "Amyloid β protein immunotherapy neutralizes Aβ oligomers that disrupt synaptic plasticity in vivo", Nature Medicine, vol. 11, No. 5, May 2005 (Published online Apr. 17, 2005), pp. 556-561.
Köhler et al., "Continuous cultures of fused cells secreting antibody of predefined specificity", Nature, vol. 256, Aug. 7, 1975, pp. 495-497.
Lewis et al., "Quantification of Alzheimer pathology in ageing and dementia: age-related accumulation of amyloid-β(42) peptide in vascular dementia", Neuropathology and Applied Neurobiology, vol. 32, 2006, pp. 103-118.
Masters et al., "Amyloid plaque core protein in Alzheimer disease and Down syndrome", Proc. Natl. Acad. Sci., vol. 82, Jun. 1985, pp. 4245-4249.
Morris, "Developments of a water-maze procedure for studying spatial learning in the rat", Journal of Neuroscience Methods, vol. 11, 1984, pp. 47-60.
Oakley et al., "Intraneuronal □-Amyloid Aggregates, Neurodegeneration, and Neuron Loss in Transgenic Mice with Five Familial Alzheimer's Disease Mutations: Potential Factors in Amyloid Plaque Formation", The Journal of Neuroscience, vol. 26, No. 40, Oct. 4, 2006, pp. 10129-10140.
Ono et al., "Structure-neurotoxicity relationships of amyloid β-protein oligomers", PNAS, vol. 106, No. 35, Sep. 1, 2009, pp. 14745-14750.
Petkova et al., "A structural model for Alzheimer's β-amyloid fibrils based on experimental constraints from solid state NMR", PNAS, vol. 99, No. 26, Dec. 24, 2002, pp. 16742-16747.
Pike et al., "Amino-terminal Deletions Enhance Aggregation of β-Amyloid Peptides in Vitro*", The Journal of Biological Chemistry, vol. 270, No. 41, Oct. 13, 1995, pp. 23895-23898.
Pillot et al., "The Nonfibrillar Amyloid β-Peptide Induces Apoptotic Neuronal Cell Death: Involvement of Its C-Terminal Fusogenic Domain", J. Neurochem., vol. 73, 1999, pp. 1626-1634.
Portelius et al., "Mass spectrometric characterization of brain amyloid beta isoform signatures in familial and sporadic Alzheimer's disease", Acta Neuropathol, vol. 120, 2010 (Published online Apr. 24, 2010), pp. 185-193.
Sawers et al., "Alternative regulation principles for the production of recombinant proteins in *Escherichia coli*", Appl. Microbiol Biotechnol, vol. 46, 1996, pp. 1-9.
Scheidt et al., "Dynamics of Amyloid β Fibrils Revealed by Solid-state NMR*", The Journal of Biological Chemistry, vol. 287, No. 3, Jan. 13, 2012, pp. 2017-2021.
Scheidt et al., "Solid-State NMR Spectroscopic Investigation of Aβ Protofibrils: Implication of a β-Sheet Remodeling upon Maturation into Terminal Amyloid Fibrils", Angewandte Chemie International Edition, vol. 50, 2011, pp. 2837-2840.

(56) References Cited

OTHER PUBLICATIONS

Tanzi et al., "Amyloid β Protein Gene: cDNA, mRNA Distribution, and Genetic Linkage Near the Alzheimer Locus", Science, vol. 235, Feb. 20, 1987, pp. 880-884.

Vorhees et al., "Morris water maze: procedures for assessing spatial and related forms of learning and memory", Nature Protocols, vol. 1, No. 2, 2006, (Published online Jul. 27, 2006), pp. 848-858.

Walsh et al., "Naturally secreted oligomers of amyloid β protein potently inhibit hippocampal long-term potentiation in vivo", Nature, vol. 416, Apr. 4, 2002, pp. 535-539.

Walsh et al., "The Oligomerization of Amyloid β-Protein Begins Intracelluarly in Cells Derived from Human Brain", Biochemistry, vol. 39, 2000 (Published online Aug. 11, 2000), pp. 10831-10839.

Wang et al., "Conformation-dependent single-chain variable fragment antibodies specifically recognize beta-amyloid oligomers", FEBS Letters, vol. 583, 2009 (Published online Jan. 20, 2009), pp. 579-584.

Wirths et al., "A modified β-amyloid hypothesis: intraneuronal accumulation of the β-amyloid peptide—the first step of a fatal cascade", Journal of Neurochemistry, vol. 91, 2004, pp. 513-520.

Wirths et al., "Identification of Low Molecular Weight Pyroglutamate Aβ Oligomers in Alzheimer Disease", The Journal of Biological Chemistry, vol. 285, No. 53, Dec. 31, 2010, pp. 41517-41524, XP-002658320.

Wirths et al., "Pyroglutamate Abeta pathology in APP/PS1KI mice, sporadic and familial Alzheimer's disease cases", J. Neural Transm., vol. 117, 2010 (Published online Oct. 13, 2009), pp. 85-96.

Wittnam et al., "Pyroglutamate Amyloid β (Aβ) Aggravates Behavioral Deficits in Transgenic Amyloid Mouse Model for Alzheimer Disease", The Journal of Biological Chemistry, vol. 287, No. 11, Mar. 9, 2012, pp. 8154-8162.

Youssef et al., "N-truncated amyloid-β oligomers induce learning impairment and neuronal apoptosis", Neurobiology of Aging, vol. 29, 2008 (Published online Apr. 24, 2007), pp. 1319-1333.

* cited by examiner

CONFORMATIONAL-SPECIFIC ANTIBODIES AGAINST A[β] OLIGOMERS

The present invention relates to a conformational specific antibody molecule directed against a conformational epitope formed by human trimeric or tetrameric Aβ oligomers, wherein said antibody molecule does not bind human monomeric Aβ 1-42 or human Aβ 1-42 dimers; and pharmaceutical and diagnostic compositions comprising said antibody molecule as well as methods using same.

BACKGROUND OF THE INVENTION

AD represents a common progressive neurodegenerative disorder that is characterized neuropathologically by extracellular deposits composed of the amyloid-β (Aβ) protein and intra-cellular accumulation of phosphorylated tau protein. The story of successful discoveries in modern AD research using novel molecular biological tools started with the biochemical analysis of β-amyloid containing blood vessels (CAA, cerebral amyloid angiopathy) and amyloid plaques consisting of Aβ, which led to the isolation and sequencing of the gene encoding the larger amyloid precursor protein (APP) (Kang, et al. (1987) *Nature* 325, 733-736; Tanzi, et al. (1987) *Science* 235, 880-884).

For more than two decades, the amyloid hypothesis has been the central hypothesis in coining the molecular pathology of AD. According to this hypothesis, amyloid fibrils, which are large insoluble polymers of Aβ found in senile plaques, are the major trigger of neuron loss and dementia typical for AD. Albeit there are convincing genetic, biochemical and cell biological data for a major role of Aβ in AD, growing evidence points towards soluble Aβ oligomers rather than Aβ precipitated in plaques.

Haass and Selkoe have recently discussed the concept that soluble oligomers of Aβ as diffusible assemblies are capable of interfering with synaptic function and integrity providing an important opening for understanding the basis of memory loss in AD. They argued that small soluble oligomers affect synaptic structure and plasticity, whereas large, insoluble plaque deposits might function as reservoirs of the pathological oligomers (Haass and Selkoe (2007) *Nat Rev Mol Cell Eliot* 8, 101-112). Moreover, it has also been suggested that the extracellular formation of Aβ plaques and other AD pathological events are preceded by intraneuronal Aβ accumulation giving rise to a modified amyloid hypothesis.

Aβ, composed of mostly 1-40 or 1-42 amino acids, is a critical component in the etiology of the neurodegenerative AD. Aβ is prone to aggregate and forms amyloid fibrils progressively both in vitro and in vivo. To understand the process of amyloidogenesis, it is pivotal to examine the initial stages of the folding process. Recently, the equilibrium folding properties, assembly states, and stabilities of the early folding stages of $Aβ_{1-40}$ and $Aβ_{1-42}$ prior to fibril formation was examined. It was found that $Aβ_{1-40}$ and $Aβ_{1-42}$ have different conformations and assembly states upon refolding from their unfolded ensembles. $Aβ_{1-40}$ is predominantly an unstable and collapsed monomeric species, whereas $Aβ_{1-42}$ populates a stable structured trimeric or tetrameric species at concentrations above ~12.5 μM. Thermodynamic analysis showed that the free energies of $Aβ_{1-40}$ monomer and $Aβ_{1-42}$ trimer/tetramer are ~1.1 and ~15/~22 kcal/M, respectively. The early aggregation stages of $Aβ_{1-40}$ and $Aβ_{1-42}$ contain different solvent-exposed hydrophobic surfaces that are located at the sequences flanking its protease-resistant segment. It was concluded that the amyloidogenic folded structure of Aβ is important for the formation of spherical β oligomeric species.

Ono and colleagues (Ono, et al. (2009) *Proc. Natl. Acad. Sci.* 106, 14745-14750) clarified the ill-defined term "oligomere" because many different ones have been reported and often existing in rapid equilibrium with monomers and higher-order assemblies. They reported results of studies in which specific oligomers have been stabilized structurally, fractionated in pure form, and then studied using different biochemical, microscopic and neurotoxicity assays. $Aβ_{1-42}$ monomers were largely unstructured, but oligomers exhibited order-dependent increases in β-sheet content. Dimerization and subsequent monomer addition are processes in which significant and asymmetric monomer conformational changes occur. Oligomer secondary structure and order correlated directly with fibril nucleation activity. Neurotoxic activity increased disproportionately (order dependence >1) with oligomer order. Their results provided significant insights into the biophysical and pathobiological behavior of Aβ, and importantly, into strategies for developing therapeutics for AD. The authors concluded that the "specific activity" of $Ab_{1-42}$ assemblies depends nonlinearly on oligomer order. In fact, $Ab_{1-42}$ dimers were reported to be 3-fold more toxic than monomers, and tetramers were 13-fold more toxic. The mechanism of toxicity is not well understood. Membrane permeabilization by amyloid oligomers may initiate a common group of downstream pathologic processes, including intracellular calcium dyshomeostasis, production of reactive oxygen species, altered signaling pathways, and mitochondrial dysfunction that represent key effectors of cellular dysfunction and cell death. Naturally secreted Aβ oligomers may directly impair synaptic function as has been shown to block hippocampal long-term potentiation (reviewed in Wirths et al. (2004) *J Neurochem* 91, 513-520).

Moreover, in vitro and in vivo analysis of amyloid deposits in AD revealed various N- and C-terminal variants. Increased C-terminal length of Aβ (from $Ab_{x-40}$ to $Ab_{x-42}$) in AD enhanced aggregation, early deposition and promoted the toxicity of Aβ. Beside Aβ peptides, starting with aspartate as the first amino acid ($Aβ_1$), several N-truncated and modified Aβ species have been described. Among Aβ species present in AD plaques, it was reported that $Aβ_{4-42}$ is a relatively abundant species in AD, aged controls and vascular dementia patients. Using immunoprecipitation in combination with mass spectrometry, Portelius and colleagues showed that $Aβ_{1-40}$, $Aβ_{1-42}$, pyroglutamate $Aβ_{pE3-42}$ and $Aβ_{4-42}$ are the dominant fractions in the hippocampus and cortex of AD patients. Interestingly, it has been demonstrated that N-terminal deletions enhance Aβ aggregation comparing $Aβ_{1-42}$ with $Aβ_{1-42}$.

Intra- or extracellular deposition of proteins is a feature of neurodegenerative diseases and serves as a molecular pathologic basis for classification as proteinopathies. While immunore-activity for Aβ or prion protein (PrP) is located predominantly extracellularly, proteins that deposit intracellularly include tau, α-synuclein, or TAR DNA Binding Protein 43 (TDP-43). Tauopathies include progressive supranuclear palsy (PSP), corticobasal degeneration (CBD), and argyrophilic grain disease (AGD), all predominated by the 4R isoform of the tau protein, and Pick's disease (PiD), a 3R tauopathy. Alpha-synucleinopathies comprise Parkinson's disease (PD), dementia with Lewy bodies (DLB), and multiple system atrophy (MSA). TDP-43 proteinopathies include a group of frontotemporal lobar degenerations (FTLD-TDP), as well as sporadic amyotrophic lateral sclerosis (ALS) cases, while the most frequent form of prion disease is sporadic Creutzfeldt-Jakob disease (CJD). Kayed et al. have reported that different types of soluble amyloid oligomers display a common conformation-dependent structure that is unique to soluble oligomers regardless of sequence suggesting that they share a common mechanism of toxicity. These conformational antibodies against Aβ also recognized non-Aβ oligomers (Kayed et al. (2003) *Science* 300, 486-489).

One of the major problems in the amyloid hypothesis is the weak correlation between the severity of dementia and the density and localization of amyloid plaques in the brain of AD patients. Memory impairment and pathological changes in many AD mouse models occur well before the onset of plaque deposition. Soluble oligomers are low molecular weight non-fibrillar structures, which are stable in aqueous solution and remain soluble even after high speed centrifugation. Aβ oligomers develop preferentially intracellularly within neuronal processes and synapses rather than within the extracellular space. On the other side, Aβ can be taken up by certain cells, and then concentrated into endosomes/lysosomes. At high concentrations, vesicular Aβ aggregates form high molecular weight oligomers which are capable of seeding amyloid fibril growth. Results from several labs propose these oligomers to be the missing link in the amyloid hypothesis. While Aβ plaques are poor correlates for the clinical symptomatology in AD and Down syndrome patients, soluble oligomers are suggested to be good predictors for synaptic loss, neurofibrillary tangles and clinical phenotype. Just like in the human brain, studies using AD mouse models support the role of oligomers. In the Tg2576 mouse model, the appearance of Aβ dodecamers coincided with the onset of spatial memory impairment. Interestingly, injection of these purified oligomers into the ventricle of wildtype rats caused a dramatic drop in spatial memory performance. With regard to short-term effects, oligomers have been shown to impair synaptic plasticity by blocking LTP and reinforcing LTD. Others generated APP transgenic mice expressing the E693Δ mutation, which causes neuronal cell death and cognitive impairment by enhanced intracellular Aβ oligomerization without plaque formation.

Therefore, oligomers are thought to be a good target for therapeutic antibodies especially that this pool represents a minor subset (around 1.4% of total Aβ) if compared to the plaque pool which occupies the whole parenchyma. Reports have shown that monoclonal antibodies raised against oligomers prevent oligomer-induced toxicity, production of reactive oxygen species, and their attachment to synapses in primary hippocampal cells. In addition, Klyubin et al. have shown that immunization against Aβ oligomers neutralized LTP inhibition induced by Aβ oligomers injected in the hippocampus of rats (Klyubin et al. (2005) *Nat Med* 11, 556-561). Cell surface receptor clustering near or within synapses might be a mechanism for oligomer toxicity in AD. Aβ oligomers can exert their toxicity through binding at synapses. It has been demonstrated that oligomers undergo a progressive shift from an extrasynaptic, freely diffusive state toward the formation of static synaptic clusters acting as an extracellular scaffold for mGluR5.

Aβ dodecamers have been described using synthetic Aβ oligomers. Dimeric Aβ was purified from AD brains and also found to inhibit LTP in hippocampal slices and induce Tau hyperphosphorylation and other degenerative effects in cultured neurons. Selkoe and others reported that toxic Aβ oligomers to be primarily dimers and trimers of Aβ (Walsh et al. (2000) *Biochemistry* 39, 10831-10839; Walsh et al. (2002) *Nature* 416, 535-539; Klyubin, et al. (2008) *J. Neurosci.* 28, 4231-4237).

Reviewed in detail by Hampel et al. (Hampel et al. (2010) *Nat Rev Drug Discov* 9, 560-574) discussed that AD biomarkers are needed to monitor drug safety, to identify individuals who are most likely to respond to specific treatments, to stratify presymptomatic patients and to quantify the benefits of treatments. Cerebrospinal fluid markers (for example, increased phosphophorylated tau and decreased $A\beta_{1-42}$ levels) are helpful as trait markers of AD that have high sensitivity and specificity. However, they explained that these biomarkers have yet to show value as markers of disease state. Of interest, it has been reported that levels of $A\beta_{1-42}$ are already fully decreased at least 5 to 10 years before conversion to AD dementia, whereas T-tau and P-tau seem to be later markers. Additionally, Aβ oligomers have also been studied as a potentially new biomarker in CSF. Analysis of HMW Aβ oligomers derived from synthetic $A\beta_{1-42}$ by size-exclusion chromatography, revealed that using an ELISA specifically detected HMW Aβ oligomers of 40-200 kDa (Fukumoto et al. (2010) *Faseb J* 24, 2716-2726). The CSF levels of these HMW Aβ oligomers showed a negative correlation with Mini-Mental State Examination scores in AD and mild cognitive patients, which are presymptomatic for AD.

Analysis of amyloid deposits in AD brains revealed various N- and C-terminal variants. The increased C-terminal length of Aβ (from $A\beta_{x-40}$ to $A\beta_{x-42}$) enhances its aggregation properties. Faster aggregation leads to earlier Aβ deposition, which is believed to promote its toxicity. Recently, $A\beta_{1-43}$ was discovered as a novel toxic peptide in AD. Besides Aβ peptides starting with aspartate as the first amino acid (Aβ1), several N-truncated and modified Aβ species have also been described. It was reported that $A\beta_{4-42}$ is a relatively abundant species in AD, aged controls and vascular dementia patients. Using immunoprecipitation in combination with mass spectrometry, it was shown that $A\beta_{1-40}$, $A\beta_{1-42}$, $A\beta_{pE3-42}$ and $A\beta_{4-42}$ are the dominant fractions in the hippocampus and cortex of AD patients. Moreover, it has been demonstrated that N-terminal deletions enhance Aβ aggregation comparing $A\beta_{4-42}$ with $A\beta_{1-42}$. It was further demonstrated that $A\beta_{1-42}$ and $A\beta_{pE3-42}$ exhibited similar effects on neuronal cytotoxicity in primary cortical neurons and on memory impairment after intracerebroventricular injection in wildtype mice. $A\beta_{pE3-42}$ is now an established factor contributing AD pathology and may even be aggravating the severity of the disease (Wittnam et al. (2012) *Journal of Biological Chemistry* 287, 8154-8162). While the possible role of $A\beta_{4-42}$ although historically discovered first and found to be a major peptide in AD brain, its role as a biomarker or therapeutic target is not well explored.

The amyloid hypothesis in Alzheimer's disease (AD) considers amyloid β peptide (Aβ) deposition as the causative event triggering down-stream events like neurofibrillary tangles, cell loss, vascular damage and memory decline. A major complication of the amyloid hypothesis has been that so far none of the antibodies therapies directed against plaque-Aβ has revealed the expected outcome in clinical trials. Although plaque load has been successfully reduced, the cognitive decline could not be influenced. Moreover, in everyday clinical practice, $A\beta_{1-42}$ ELISAs are used that do not discriminate between the different aggregation states (monomers up to high molecular weight oligomers (HMW)) and are lowered during the development of AD.

In view of the above, it is desirable to target all $A\beta_{x-42}$ low and high molecular weight oligomers specifically. The expected therapeutic benefit is to neutralize these oligomers by passive immunization as has been demonstrated recently for another oligomer-specific antibody 9D5 detecting only low molecular weight (LMW) $A\beta_{pE3-42}$ (Wirths et al. (2010) *J. Biol. Chem.* 285, 41517-41524; and WO 2011/151076). Other antibodies specific for $A\beta$-peptides and certain oligomers are described in WO 2009/056490, U.S. Pat. No. 7,763,249, EP 2 210 901, and EP 2 246 427.

WO 2009/065054 discloses antibodies specific for the protofibril form of $A\beta$-peptides (~670 kDA). However, these antibodies differ from the presently described ones, since the antibodies of WO 2009/065054 do not bind to trimeric or tetrameric human $A\beta$, i.e. low molecular weight forms of $A\beta$-oligomers (cf. FIGS. 1, 2A, and 3A of WO 2009/065054). Wang et al. (Wang et al. (2009) *FEBS Letters* 583, 579-584) disclose scFv's W8, W9, W20, and WC2, which bind to $A\beta$ trimers, tetramers and little bigger oligomers. However, the exact epitope, and/or the sequence of the variable regions of these antibody molecules are not described.

Kim et al. (Kim et al. (2004) *Neurobiology of Aging* 25, S145) describe the synthesis of conformationally-defined $A\beta$ haptens, which may be useful for a future selection of antibodies that can selectively sequester these folding intermediates.

Presently, it is an object of the invention to provide novel antibodies, which can be advantageously used in the treatment and diagnosis of AD.

SUMMARY OF THE INVENTION

Together with full-length $A\beta_{1-42}$, N-truncated pyroglutamate $A\beta_{pE3-42}$ and $A\beta_{4-42}$ are major variants in AD brain. The inventor has identified antibodies that, due to its common epitope, react not only with HMW $A\beta_{1-42}$, but also with its major N-truncated variants $A\beta_{pE3-42}$ and $A\beta_{4-42}$ opening the potential to develop more sensitive biomarkers for diagnosing AD and monitoring drug efficacy in clinical trials. The present invention demonstrates the first successful attempt to identify an epitope that differentiates $A\beta_{1-42}$ tri- or tetramers from $A\beta_{1-42}$ mono- and dimers. It is known for several years that $A\beta_{1-42}$ tri- or tetramers are the most toxic $A\beta$ peptides at the beginning of the pathology of AD.

In particular, two novel conformational specific $A\beta$ antibodies NT4X-83 and NT4X-167 preferentially reacting with N-truncated $A\beta_{4-42}$ were developed having a unique binding pattern: NT4X recognized low and high molecular weight oligomers of $A\beta_{1-42}$, $A\beta_{4-42}$ and $A\beta_{pE3-42}$, with the highest preferences for $A\beta_{4-42}$. NT4X detected only a minor portion of plaques in sporadic and familial AD cases and AD mouse models and did not cross-react with other aggregates typical for other common neurodegenerative diseases showing that NT4X staining is specific for AD. Importantly, NT4X inhibited aggregation and toxicity of $A\beta_{1-42}$, $A\beta_{4-42}$ and $A\beta_{pE3-42}$ implicating their potential for AD therapy.

Having two specific antibodies developed, it is now possible to target these oligomers specifically. The expected therapeutic benefit is to neutralize the toxic $A\beta$-oligomers by passive immunization for example.

Thus, in summary,

The antibodies of the invention recognize a conformational epitope formed by the amino acids in position four and five of $A\beta$, in particular phenylalanine at position four of $A\beta$.

The antibodies according to the invention differentiate $A\beta_{1-42}$ LMW oligomers from $A\beta_{1-42}$ mono- and dimers.

The antibodies according to the invention bind native LMW oligomers derived from $A\beta_{pE3-42}$ and most efficiently $A\beta_{4-42}$.

Aged $A\beta_{1-42}$, $A\beta_{pE3-42}$ and $A\beta_{4-42}$ develop HMW oligomers detected by the antibodies according to the invention. $A\beta_{3-38}$ and $A\beta_{4-40}$ did not aggregate into HMW oligomers.

The antibodies according to the invention rescued toxic effects of all $A\beta$ peptides tested using cell viability and aggregation assays in vitro and detected only a minor fraction of plaques in brain from sporadic and familial AD patients and two transgenic mouse models of AD. As the amount of detected plaques by the antibodies according to the invention is minor, an adverse treatment effect by passive immunization by dissolving plaques is not likely and side effects are not expected. The antibodies according to the invention are therefore expected to be highly valuable in the treatment of AD.

The antibodies according to the invention specifically reacted with blood vessel walls and with intraneuronal $A\beta$. Hence, two assumptions can be made: 1. These oligomers are soluble. 2. These oligomers likely can be found in sufficient amounts in blood making a blood test for AD possible. Further, they did not cross-react with aggregates typical for other major neurodegenerative disorders implicating that the recognized aggregates are disease-specific for AD. Therefore, the antibodies according to the invention are highly valuable for diagnostic purposes.

Accordingly, in a first aspect, the invention relates to a monoclonal antibody molecule recognizing a conformational epitope formed by Phe at amino acid position 4 of human $A\beta$ in trimeric or tetrameric $A\beta$ oligomers, wherein said antibody molecule does not bind human monomeric $A\beta$1-42 or human $A\beta$1-42 dimers, as determined by native Western-blotting using 7 μg $A\beta$ 1-42 on a 18% SDS-free polyacrylamide gel and 0.45 nitrocellulose membranes and said antibody molecule as the primary antibody in a concentration of not to more than 10 μg/ml.

The antibody molecule is particularly useful for use in medicine or veterinary medicine, in particular for use in the treatment and/or prevention of Alzheimer's disease, in particular wherein the Alzheimer's disease is sporadic Alzheimer's disease or familial Alzheimer's disease. Accordingly, the invention also relates to the use of an antibody molecule according to the first aspect in the manufacture of a medicament.

In a related aspect, the invention further provides a method of treating or preventing Alzheimer's disease in a subject, comprising the step of administering an antibody molecule according to the first aspect to said subject.

In still another aspect, the invention relates to the use of the antibody molecule according to the first aspect in a method of diagnosing Alzheimer's disease, or in a method of identifying agents useful in the treatment and/or prevention of Alzheimer's disease, in particular wherein the Alzheimer's disease is sporadic Alzheimer's disease or familial Alzheimer's disease.

Thus, in another aspect, the invention relates to a method of diagnosing Alzheimer's disease, comprising the step of determining the amount of low molecular weight oligomers of $A\beta$ in a sample of a subject to be diagnosed, using an antibody molecule according to the invention. In this context, the invention also pertains to a diagnostic composition comprising an antibody molecule according to the invention.

The invention further relates to the use of an antibody molecule according to the first aspect in a method of monitoring the efficacy of a treatment of Alzheimer's disease, in particular wherein the Alzheimer's disease is sporadic Alzheimer's disease or familial Alzheimer's disease. Accordingly, the invention also relates to a method of monitoring the efficacy of a treatment of Alzheimer's disease, comprising the step of determining the amount of low molecular weight oligomers of Aβ in a sample of a subject to be diagnosed using an antibody molecule according to the invention.

In still another aspect, the invention also pertains to a hybridoma as deposited under DSM ACC3161 or hybridoma as deposited under DSM ACC3162, which produces an antibody according to the first aspect.

Likewise, the invention further provides a nucleic acid molecule encoding the antibody molecule according to the first aspect, a vector comprising said nucleic acid molecule, and a host cell comprising said nucleic acid molecule or said vector.

In a final aspect, the invention also relates to a method of producing an antibody molecule according to the first aspect comprising the step of (i) culturing the host cell or the hybridoma of the invention under conditions allowing synthesis of said antibody molecule and (ii) recovering said antibody molecule from said culture.

DETAILED DESCRIPTION OF THE PREFERRED EMBODIMENTS

In a first aspect, the invention relates to a monoclonal antibody molecule recognizing a conformational epitope formed by Phe at amino acid position 4 of trimeric or tetrameric human Aβ, as determined by pepscan ELISA comprising the steps of precoating with 100 ng $Aβ_{4-19}$ and $Aβ_{5-20}$, blocking, incubating with 7 µg/ml of said antibody molecule, and detecting said antibody molecule with a labeled secondary antibody; wherein said antibody molecule does not bind human monomeric $Aβ_{1-42}$ or human $Aβ_{1-42}$ dimers, as determined by native Western-blotting comprising the steps of applying 7 µg $Aβ_{1-42}$ on a 18% SDS-free polyacrylamide gel, transferring on a 0.45 µm nitrocellulose membrane, blocking, incubating with said antibody molecule in a concentration of not more than 10 µg/ml for 2 h at room temperature, and detecting said antibody molecule with a labeled secondary antibody.

The term "monoclonal antibody molecule" as used herein refers to an antibody molecule derived from a population of substantially homogeneous antibodies, i.e. the individual antibody molecules comprised in the population are identical except for possible naturally occurring mutations that may be present in minor amounts. Typically, monoclonal antibody molecules are highly specific and are directed against a single epitope. In addition to their specificity, the monoclonal antibody molecules may be advantageously synthesized uncontaminated by other antibodies. The modifier "monoclonal" is not to be constructed as requiring production of the antibody molecule by any particular method. However, a monoclonal antibody molecule as disclosed herein may be produced by the hybridoma method first described by Kohler, G. et al., Nature 256 (1975) 495, or by recombinant DNA methods (see, e.g., U.S. Pat. No. 4,816,567).

An example of the antibody molecule of the first aspect is an antibody produced by hybridoma as deposited under DSM ACC3161 or hybridoma as deposited under DSM ACC3162. Likewise, the antibody molecule may be an antibody molecule which competes for the same epitope with antibody NT4X-83, as deposited under DSM ACC3161, and/or antibody NT4X-167, as deposited under DSM ACC3162. Assays for determining competitive binding of two antibodies are known in the art. For example, a competitive assay may be based on the pepscan ELISA assay, as described below, wherein the human Aβ 1-42 is preincubated with NT4X-83 or NT4X-167, and subsequent binding of the competing antibody molecule is detected using a detection antibody, which is specific for said competing antibody molecule. Alternatively, the human Aβ 1-42 is preincubated with the competing antibody molecule, and subsequent binding of NT4X-83 or NT4X-167 is detected using a detection antibody, which is specific for NT4X-83 or NT4X-167.

The antibody molecule may be a recombinant full antibody (immunoglobulin), a F(ab)-fragment, a $F(ab)_2$-fragment, a F(v)-fragment, a single-chain antibody, a chimeric antibody, a CDR-grafted antibody, a bivalent antibody-construct, a polyvalent antibody-construct, a synthetic antibody, a cross-cloned antibody, a fully-human antibody, a humanized antibody, nanobodies, and polyvalent nanobodies or diabodies.

Antibodies are also called immunoglobulins. They are gamma globulin proteins and generally consist in their natural form of two heavy chains and two light chains linked by disulfide bonds. Five types of mammalian Ig heavy chains are known: α, δ, ε, γ, and µ, wherein the type of heavy chain defines the class (isotype) of the antibody, which are IgA, IgD, IgE, IgG, and IgM. The heavy chain contains two regions, the constant region and the variable region. The constant region shares high homology in all naturally occurring antibodies of the same isotype within the same species. Like the heavy chain, a light chain also consists of one constant domain and one variable domain. In mammals there are two types of immunoglobulin light chain, lambda (λ) and kappa (κ). The unique property or specificity of a given antibody is determined by the variable (V) regions. In particular, three variable loops in each the light ($V_L$) and the heavy ($V_H$) chain, are responsible for the antigen specificity.

The term "full antibody" is intended to refer to any antibody that has a typical overall domain structure of a naturally occurring antibody (i.e. comprising a heavy chain of three or four constant domains and a light chain of one constant domain as well as the respective variable domains). Nevertheless, each domain may comprise further modifications, such as mutations, deletions, or insertions, which do not change the overall domain structure. The antibody may be an IgA, IgD, IgE, IgG, or IgM antibody, including any subclass of these isotypes. In one preferred embodiment, the antibody is an IgG antibody, such as an IgG1 or IgG2 antibody. If recombinantly produced, the antibody may also comprise two different constant regions of heavy chains, e.g. one IgG1 and one IgG2 heavy chain, or heavy chains from different species. The heavy chains are, however, preferably from the same species.

A fragment of an antibody molecule contains at least one antigen binding fragment as defined above, and exhibits the same specificity as the complete antibody of which the fragment is derived from, e.g. an antibody fragment of NT4X-83 or NT4X-167 has the same specificity than the NT4X-83 or NT4X-167 antibody. Methods of producing antibody molecule fragments are known in the art. For example, Fab fragments may be generated from an immunoglobulin by using the enzyme papain. Likewise, $F(ab)_2$ fragments are formed by using the enzyme pepsin, which cleaves below the hinge region and, thus, below the disulfide bonds. Alternatively, the variable regions of the heavy and light chains can be fused together to form a single chain variable fragment (scFv). Thus, in the context of the this invention, an antibody molecule does also comprise variable and light regions, F(ab)-, F(ab)$_2$ fragments, CDR-regions, etc. of the antibody molecule as disclosed herein. The antibody molecule may also be a humanized or CDR-grafted antibody molecule, as well as genetically/recombinantly engineered. An example of an engineered antibody molecule, e.g. produced by CDR-grafting, is an antibody, in which at least one region of an immunoglobulin of one species is fused to another region of an immunoglobulin of another species in order to reduce its immunogenicity. CDR-grafting is well-known in the art. Alternatively, the antibody molecule may be a fully-human antibody. One variable region of the antibody molecule of the invention may also be combined with another variable region, which binds to another epitope, thereby generating bivalent or polyvalent antibody constructs. Also provided are derivatives of such antibody molecules, like single-chain antibodies, diabodies, bispecific single chain antibodies, nanobodies and polyvalent nanobodies.

The antibody molecule recognizes a conformational epitope, which is predominantly formed by Phe at amino acid position 4 of human Aβ of each of the Aβ forming trimeric and/or tetrameric oligomers. Generally, a conformational epitope is a formation of subunits, here human Aβ, composing an antigen that is recognized by an antibody molecule. "Predominantly" is thereby intended to mean that said Phe is a prerequisite for detection with high intensity of binding to human Aβ, as also demonstrated in the examples section, where the antibody molecule showed binding to Aβ$_{4-19}$ but not to Aβ$_{5-20}$. However, in a preferred embodiment, the epitope further comprises the amino acids at position 2 and 3 of human Aβ, as determined by pepscan ELISA. Pepscan is a procedure for mapping and characterizing epitopes involving the synthesis of overlapping peptides and analysis of the peptides in enzyme-linked immunosorbent assay (ELISAs).

Aβ peptides with 16 amino acids in length may be used: Aβ$_{1-16, 2-17, 3-18, 4-19, 5-20, 6-21, 7-22, 8-23, 9-24}$ and $_{10-25}$. The experiment is performed using U form high binding 96 well-plate (microplates, Greiner bio-one) to coat the peptides. Samples are diluted in ice cold sterile-filtered 0.05 M carbonate buffer (2.4 g NaCO$_3$×10H$_2$O, 1.46 g NaHCO$_3$ added to 450 ml ddH$_2$O, pH 9.6) and 50 µl of the diluted samples are coated on the wells (the well-plate is kept on ice for some min before peptide application). For the peptide binding, the well-plate is incubated overnight at 4° C. The next day, the wells are washed three times by 0.01 M PBS (RT). The washing is done by applying 250 µl PBS into each well and emptying it by inverting the plate and hit it hard on a spongy cloth. After the washing step, three other steps are conducted (each step for 1 h at 25° C.): blocking (preventing unspecific antibody binding); incubation with primary antibody, i.e. the antibody molecule to be tested, at a concentration of 7 µg/ml; incubation with the secondary antibody (e.g., HRP coupled goat anti-mouse IgG, Dianova, 1:10.000, cat no: 115-035-003; or a labeled secondary antibody recognizing the κ or λ light chain). The skilled person will know how to choose a suitable secondary antibody. After each mentioned step, three times washing with 0.01 M PBS is applied. For the blocking step, 200 µl of the RT blocking solution containing 5% w/v Albumin Fraction V (Roth) in 0.01 M PBS, which is prepared, sterile filtered and kept at 4° C. a day before use. Both, primary and secondary antibodies, are diluted in the blocking solution and 100 µl of each dilution is used for each well. Lastly, as a HRP enzyme substrate, 50 µl of 3,3',5,5'-Tetramethylbenzidin (1-step Ultra TMB ELISA substrate, Thermo Scientific), that leads to the blue color production when oxidized, is added to each of the wells and the absorbance (OD) is measured within 5-10 min at 652 nm by a microplate reader (pQuant, BTek Instrument INC) using Mikro Win 2000 software (Berthold Technologies). The reaction is stopped by adding 50 µl of 2 M, H$_3$PO$_4$ which leads to yellow color formation and the absorbance is measured at 450 nm.

The affinity constant for binding of an antibody molecule to the epitope formed by the trimeric or tetrameric Aβ oligomers can span a wide range, extending from about $10^5$ mol$^{-1}$ to about $10^{12}$ mol$^{-1}$, and the affinity constant is preferably at least $10^6$ mol$^{-1}$, more preferably at least $10^7$ mol$^{-1}$, even more preferably at least $10^8$ mol$^{-1}$, most preferably at least $10^9$ mol$^{-1}$, and even most preferably at least $10^{10}$ mol$^{-1}$, such as at least $10^{11}$ mol$^{-1}$. Procedures for determining an affinity constant of an antibody molecule are known in the art.

The antibody molecule recognizes a conformational epitope formed in trimeric or tetrameric Aβ oligomers. The Aβ oligomers may be composed of a single type of Aβ, or of a mixture of one, two, three, or more types of Aβ. In a preferred embodiment, the trimeric or tetrameric Aβ oligomers are oligomers of Aβ 1-X, Aβ 4-X, and/or pyro-Glu-Aβ 3-X, wherein X is 42, 40 or 38, preferably wherein X is 42. In one preferred embodiment, the Aβ oligomers are oligomers of Aβ 1-42. In another preferred embodiment, the Aβ oligomers are oligomers of Aβ 1-40. In another preferred embodiment, the Aβ oligomers are oligomers of Aβ 1-38. In another preferred embodiment, the Aβ oligomers are oligomers of Aβ 4-42. In another preferred embodiment, the Aβ oligomers are oligomers of Aβ 4-40. In another preferred embodiment, the Aβ oligomers are oligomers of Aβ 4-38. In another preferred embodiment, the Aβ oligomers are oligomers of pyro-Glu-Aβ 3-42. In another preferred embodiment, the Aβ oligomers are oligomers of pyro-Glu-Aβ3-40. In another preferred embodiment, the Aβ oligomers are oligomers of pyro-Glu-Aβ 3-38.

As discussed in the background of the invention section, Ono, et al. reported results of studies in which specific oligomers have been stabilized structurally, fractionated in pure form, and then studied using different biochemical, microscopic and neurotoxicity assays. It could be demonstrated that Aβ$_{1-42}$ monomers were largely unstructured, but oligomers exhibited order-dependent increases in β-sheet content. Dimerization and subsequent monomer addition are processes in which significant and asymmetric monomer conformational changes occur, thereby generating an epitope which is specifically bound by the antibody molecule of the invention under native conditions. Ono et al. reported that Aβ$_{1-42}$ dimers were 3-fold more toxic than monomers, and tetramers were even 13-fold more toxic. In fact, it is known for several years that Aβ$_{1-42}$ tri- or tetramers are the most toxic Aβ peptides at the beginning of the pathology of AD. Accordingly, the amount of trimers and tetramers of Aβ in a sample are considered being predictive of disease state and disease progression. The antibody molecule according to the invention is capable of differentiating between Aβ$_{1-42}$ monomers and dimers on the one hand, and Aβ$_{1-42}$ trimers and tetramers on the other hand. Accordingly, due to its specificity for the specific epitope identified herein, the antibody is not adsorbed to the less toxic monomers and dimers, and even shows very low binding to plaques. Due to these surprising characteristics, the antibody molecule according to the invention is particularly useful in diagnosis, treatment and prophylaxis of diseases associated with human Aβ, in particular $Aβ_{1-42}$, such as Alzheimer's disease.

In order to determine whether an antibody molecule binds $Aβ_{1-42}$ tri- or tetramers but not the respective monomers and dimers, one may conduct native Western-blotting comprising the steps of applying 7 μg $Aβ_{1-42}$ on a 18% SDS-free polyacrylamide gel, transferring on a 0.45 μm nitrocellulose membrane, blocking, incubating with said antibody molecule in a concentration of not more than 10 μg/ml, preferably 5-10 μg/ml, such as 6-9 μg/ml, e.g. 7 or 8 μg/ml, for 2 h at room temperature, and detecting said antibody molecule with a labeled secondary antibody. The secondary antibody may be any suitable secondary antibody, which is capable of recognizing the antibody molecule of the invention, e.g. by binding to its Fc-portion or to the light chain, or to another polypeptide, which was introduced into the antibody molecule by way of a fusion polypeptide in order to provide a specific antigenic epitope. The secondary antibody is usually labeled with a marker, dye or enzyme, which allows a quantitative detection of a signal which correlates with the binding of the secondary antibody to the antibody molecule, and thus with the binding of the antibody molecule to the conformational epitope.

More specifically, the peptides are mixed with the dye (Tris-Glycin Native Probenpuffer, Anamed) in the ration of 1:1 for 5 min at RT. Then, the sample is loaded on 18% SDS-free gels (Progel Tris Glycin 18%, 1.0 mm, Anamed). Running the proteins on the gel is done using the SDS-free running buffer (Tris-Glycin Native Laufpuffer Anamed). The proteins are then transferred on 0.45 μm nitrocellulose membrane (GE Healthcare), using the semi-dry method (Bio RAD, Trans- Blot® SD Semi-Dry): The membrane, gel and two thick blotting papers are wetted into the transfer buffer (48 mM Tris-HCL buffer, 39 mM glycin (5% methanol) pH 9.2). Wet thick papers are placed around the membrane and the gel (the membrane was lying under the gel) and the protein transfer is performed at 25 V for 1 h (Trans-Blot® SD semi-dry Transfer cell, BIO-RAD). Upon completion of protein transfer, the membrane is washed two times each for 10 min in 1× TBS/T (0.1 M Tris, 1.5 M NaCl and 0.5% Tween 20) on a rotator (Heidolph, DOUMAX 1030) with speed of 40 rpm. For Aβ peptides, membranes are boiled in 0.1 M PBS for about 1 min in microwave (ShARP) on 800 Watt power. After the start of boiling, the power is decreased to 80 Watt and the boiling is continued for 4 more minutes. Membranes are briefly washed in 1× TBS/T and blocked with 10% non-fat dry milk (Roth) in 1× TBS/T for 1 h at room temperature (RT) (40 rpm shaking). The membrane is incubated with following primary antibodies overnight at 4° C. or 2 h at RT (40 rpm shaking). This step is followed by two times of washing with 1× TBS/T each for 10 min (40 rpm shaking) and the membrane is incubated with secondary antibody (e.g. Polyclonal goat anti-mouse, Dianova diluted 1:4000) conjugated with horseradish peroxidase, for 2 h at RT. The skilled person will know how to choose an appropriate secondary antibody. After washing for two times, each for 10 min, for development, the membrane is incubated in the horseradish peroxidase substrate solution containing 8 ml solution A (0.25 mg/ml luminal (Roth) in 0.1 M Tris/HCl), 800 μl solution B (1.1 mg/ml para-coumaric (Roth) acid in DMSO (Sigma) and 2.5 μl $H_2O_2$ (Roth) for 2 min. After slightly drying the membrane on a tissue paper, it is exposed to x-ray films (Hyperfilm EC, Amersham Biosciences) for different time points and developed in a CUR1x60 (AGFA). Further guidance can be found in the examples section.

The inventor observed a striking difference between the binding of NT4X with Aβ peptides under reducing and native conditions. While under reducing conditions, LMW oligomers of $Aβ_{1-42}$, $Aβ_{pE3-42}$ and $Aβ_{4-42}$ were detected, a strong signal was seen for monomers of $Aβ_{pE3-42}$ and $Aβ_{4-42}$, but not $Aβ_{1-42}$. Under reducing conditions, $Aβ_{1-42}$, $Aβ_{pE3-42}$ and $Aβ_{4-42}$ formed stable LMW oligomers after dissolving the peptides. Aging of the peptides resulted in a shift of the SDS-stable signal $Aβ_{1-42}$, $Aβ_{pE3-42}$ and $Aβ_{4-42}$ to HMW oligomers. No difference was observed between under reducing and native conditions for $Aβ_{4-38}$ and $Aβ_{4-40}$, which apparently only formed monomers and dimers. Accordingly, as shown in the examples, the antibody molecule in accordance with the invention may not only bind oligomers of low order, but also "aged Aβ polypeptides", i.e. HMW oligomers of Aβ 1-42, pyro-Glu-Aβ3-42 and/or Aβ4-42, as determined by native Western-blotting using 18% SDS-free polyacrylamide gel and 0.45 nitrocellulose membranes and said antibody molecule as the primary antibody in a concentration of not more than 10 μg/ml, preferably 5-10 μg/ml, such as 6-9 μg/ml, e.g. 7 or 8 μg/ml. The native western blot assay may be conducted as described above.

As discussed above, the antibody molecule recognizes aggregates that are specific for Alzheimer's disease. For example, the antibody molecule recognizes aggregates in immunohistochemistry of brain tissue sections, in particular wherein the Alzheimer's disease is familial Alzheimer's disease. The immunohistochemistry may be carried out as follows: 4 μm brain sections are obtained by cutting paraffin-embedded brain tissue using a microtome. Deparaffinization is performed by incubation in xylol (Carl Roth GmbH) two times each for 5 min and followed by series of decreasing ethanol (Chemie-vertrieb) concentration (100%, 95% and 70% for 10, 5 and 3 min respectively) to rehydrate the sections. This stage is followed by 1 min washing the sections with deionized $H_2O$. Endogenous peroxidase blocking is achieved by incubation of the sections for 30 min in the solution of 200 ml 0.01 M PBS and 2 ml 30% $H_2O_2$. Sections are washed by deionized $H_2O$ for 1 min. The antigen retrieval is performed by boiling the sections in 10 M Citrate buffer (4.2 g Citric acid-Monohydrate added to 2000 ml $H_2O$; pH=6) for 2 min in a microwave at 800 Watt power. After 2 min the power is decreased to 80 Watt and the boiling is continued for additional 8 min. After cooling down the sections for 15 min they are washed with deionized $H_2O$ for 1 min followed by incubation in 0.01 M PBS+0.1% Triton for 15 min and for 1 min incubation in 0.01 M PBS as washing step. Incubation with freshly prepared 88% formic acid for 3 min followed. Sections are washed twice by 0.01 M PBS for 1 and 5 min. Unspecific blocking is done by 1 h in 4% milk powder (Roth), 10% fetal cow serum (FCS) in 0.01 M PBS in wet a chamber at RT. Primary antibodies, diluted in 0.01 M PBS and 10% FCS, are applied on the sections and are incubated at RT overnight (in a wet chamber). On the next day, sections are washed three times, each for 5 min by 0.01 M PBS+0.1% Triton and for 1 min by 0.01 PBS. Then, secondary antibody (Rabbit anti-mouse, Dako, cat. no. E0354), conjugated with biotin is diluted 1:200 in 0.01 PBS and 10% FCS and is applied on the sections in the wet chamber and incubated for 1 h at 37° C. This step is followed by Avidin-Biotin complex (ABC) (Vectastain® Elite ABC Kit, Vector Laboratories; cat. No. PK6100) incubation at 37° C. for 1.5 h which is prepared and kept at 4° C. at least 30 min before its application. ABC solution is prepared as followed: 0.01 M PBS+10% FCS+ 1:100 solution A+1:100 solution B. Afterwards, the sections are washed three times with 0.01 PBS each time for 5 min, and the sections are exposed to diaminobenzidine (DAB) solution (5 ml 50 mM Tris/HCl PH 7.5+100 µl DAB stock solution (25 mg/ml 5-(4-Dimethylamino-Benzylidene)Rhodanine (sigma) in 0.05 M Tris/HCL, PH 7.4)+2.5 µl 30% $H_2O_2$ (Roth) (added right before use) for a few minutes until staining was observed. The sections are washed with 0.01 PBS, three times each time for 5 min, and counterstaining is performed using filtered hematoxylin, for 40 s. The sections are dipped into deionized $H_2O$ and then washed in running tap water for 5 min. As the last step in staining, sections are dehydrated by series of increasing ethanol concentration (1 min 70%, 5 min 95% and 10 min 100%) and in the end two times in xylol, each for 5 min. The sections, then, are embedded using eukitt quick hardening mounting medium (Carl Roth GmbH (Roti®-Histokit)). However, the antibody molecule may also be used in other types of assays, such as in a quantitative assay for determining the amount of trimeric and tetrameric oligomers of human Aβ in e.g. body fluids such as blood, serum or spinal fluid, for example by way of an ELISA.

In another preferred embodiment, the antibody molecule inhibits further aggregation of trimeric or tetrameric Aβ oligomers of Aβ 1-X, Aβ 4-X, and/or pyro-Glu-Aβ 3-X, wherein X is 42, 40 or 38, preferably wherein X is 42, when tested in a concentration of 10 µM in 50 mM sodium phosphate buffer, 50 mM NaCl, 20 µM thioflavin T and 0,01% sodium azide, pH 7.4, at 37° C. in a peltier adapter with stirring in a thioflavin T aggregation assay. In one preferred embodiment, the Aβ oligomers are oligomers of Aβ 1-42. In another preferred embodiment, the Aβ oligomers are oligomers of Aβ 1-40. In another preferred embodiment, the Aβ oligomers are oligomers of Aβ 1-38. In another preferred embodiment, the Aβ oligomers are oligomers of Aβ 4-42. In another preferred embodiment, the Aβ oligomers are oligomers of Aβ 4-40. In another preferred embodiment, the Aβ oligomers are oligomers of Aβ 4-38. In another preferred embodiment, the Aβ oligomers are oligomers of pyro-Glu-Aβ 3-42. In another preferred embodiment, the Aβ oligomers are oligomers of pyro-Glu-Aβ 3-40. In another preferred embodiment, the Aβ oligomers are oligomers of pyro-Glu-Aβ 3-38.

Aβ peptides are solubilized in 10 mM NaOH at a concentration of 1 mg/ml, sonicated for 5 min, frozen in liquid nitrogen, and stored at −80° C. until use. Aggregation of Aβ peptides is investigated online using ThT aggregation assay (Varian fluorescence spectrophotometer) is using an excitation wavelength of 446 nm and emission wavelength of 482 nm. Samples contain 10 µM of Aβ, 50 mM sodium phosphate buffer (pH 7.4), 50 mM NaCl, 20 µM ThT and 0.01% sodium azide. The samples are incubated at 37° C. in a peltier adapter with stirring. Data points are recorded every 10 min during the assay and plotted in a diagram time [min] vs. fluorescence [a.u.]. If the antibody molecule is capable of inhibiting Aβ-oligomerization, the graph will reach a plateau phase, in which the oligomers are "stabilized" by the binding molecule, and do not further oligomerize and aggregate. In the context of the present invention, an antibody molecule is capable of inhibiting Aβ-oligomerization, if the resulting graph shows no inflection point after 250 min, preferably after 300 min, more preferably after 350 min, even more preferably after 400 min, such as after 450 min, and most preferably after 500 min incubation time.

An example of an antibody molecule in accordance with the present invention is the NT4X-83 and NT4X-167 antibody. Said antibodies are producible from and deposited as hybridomas. Thus, the invention also relates to a hybridoma as deposited under DSM ACC3161 or hybridoma as deposited under DSM ACC3162. Methods for producing the NT4X-83 and NT4X-167 antibody are also described below.

The sequences of the CDRs and the variable regions of the light and heavy chains of the NT4X-83 and NT4X-167 antibodies are provided below under the section sequences. Based on the provided sequences and on the antibodies as obtainable and deposited as a hybridoma under DSM ACC3161 and DSM ACC3162, the skilled person can readily design further antibody molecules having the desired properties described above. Accordingly, in a preferred embodiment, the antibody molecule comprises a variable region that comprises a H-CDR1, a H-CDR2 and a H-CDR3 as shown in SEQ ID NOs: 1, 2 and 3, and a L-CDR1, a L-CDR2 and a L-CDR3 as shown in SEQ ID NOs: 4, 5 and 6 (NT4X-83). In another preferred embodiment, the antibody molecule comprises a variable region that comprises a H-CDR1, a H-CDR2 and a H-CDR3 as shown in SEQ ID NOs: 9, 10 and 11, and a L-CDR1, a L-CDR2 and a L-CDR3 as shown in SEQ ID NOs: 12, 13 and 14 (NT4X-167). However, useful antibody molecules may also be obtained, which comprise a variable region that comprises a H-CDR1, a H-CDR2 and a H-CDR3 as shown in SEQ ID NOs: 1, 2 and 3 (NT4X-83). In still another to preferred embodiment, the antibody molecule comprises a variable region that comprises a H-CDR1, a H-CDR2 and a H-CDR3 as shown in SEQ ID NOs: 9, 10 and 11 (NT4X-167). Likewise, the antibody molecule may comprise a variable region that comprises a L-CDR1, a L-CDR2 and a L-CDR3 as shown in SEQ ID NOs: 4, 5 and 6 (NT4X-83). In still another preferred embodiment, the antibody molecule comprises a variable region that comprises a L-CDR1, a L-CDR2 and a L-CDR3 as shown in SEQ ID NOs: 12, 13 and 14 (NT4X-167).

The antibody molecule may also be defined by reference to a sequence of a complete variable region. It is most preferred that such variable regions comprise the CDRs and/or combination of CDRs given above. Alternatively, a particular combination of CDRs set forth above differs not more than in ten amino acid residues, such as 9 amino acid residues, preferably 8 amino acid residues, such as 7 amino acid residues, more preferably 6 amino acid residues, such as 5 amino acid residues, even more preferably 4 amino acid residues, such as 3 amino acid residues, and most preferably in 2 amino acid residues, such as 1 amino acid residue from the combination of sequences taken together.

Hence, in one preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 7, and comprising an amino acid sequence which is at least 80%, preferably 85%, more preferably 90%, even more preferably 95%, most preferably 97%, such as 100% identical to the amino acid sequence as shown in SEQ ID NO: 8 (NT4X-83).

In another preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 15, and comprising an amino acid sequence which is at least 80%, preferably 85%, more preferably 90%, even more preferably 95%, most preferably 97%, such as 100% identical to the amino acid sequence as shown in SEQ ID NO: 16 (NT4X-167).

In still another preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 7 (VH NT4X-83).

In another preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 15 (VH NT4X-167).

In another preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 8 (VL NT4X-83).

In another preferred embodiment, the antibody molecule comprises a variable region comprising an amino acid sequence which is at least 80%, preferably 85%, more preferably 90%, even more preferably 95%, most preferably 97%, such as 100% identical to the amino acid sequence as shown in SEQ ID NO: 16 (VL NT4X-167).

The person skilled in the art is readily in a position to verify the sequence identity of sequences, e.g. by simply comparing said sequences over the whole length of the sequence provided herein. For example, such an alignment can be performed using publicly available computer homology programs such as the "BLAST" program provided at the NCBI homepage, using the default settings provided therein. Further methods of calculating sequence identity percentages of sets of amino acid sequences are known in the art.

Therefore, one aspect of the invention relates to an antibody molecule comprising
(a) a variable region that comprises a H-CDR1, a H-CDR2 and a H-CDR3 as shown in SEQ ID NOs: 1, 2 and 3, and a L-CDR1, a L-CDR2 and a L-CDR3 as shown in SEQ ID NOs: 4, 5 and 6 (NT4X-83); or
(b) a variable region that comprises a H-CDR1, a H-CDR2 and a H-CDR3 as shown in SEQ ID NOs: 9, 10 and 11, and a L-CDR1, a L-CDR2 and a L-CDR3 as shown in SEQ ID NOs: 12, 13 and 14 (NT4X-167); or
(c) a variable region that comprises a H-CDR1, a H-CDR2 and a H-CDR3 as shown in SEQ ID NOs: 1, 2 and 3 (NT4X-83); or
(d) a variable region that comprises a H-CDR1, a H-CDR2 and a H-CDR3 as shown in SEQ ID NOs: 9, 10 and 11 (NT4X-167); or
(e) a variable region that comprises a L-CDR1, a L-CDR2 and a L-CDR3 as shown in SEQ ID NOs: 4, 5 and 6 (NT4X-83); or
(f) a variable region that comprises a L-CDR1, a L-CDR2 and a L-CDR3 as shown in SEQ ID NOs: 12, 13 and 14 (NT4X-167).

In a preferred embodiment, said antibody molecule comprises
(a) a variable region comprising an amino acid sequence which is at least 80%, preferably 85%, more preferably 90%, even more preferably 95%, most preferably 97%, such as 100% identical to the amino acid sequence as shown in SEQ ID NO: 7, and comprising an amino acid sequence which is at least 80% identical to the amino acid sequence as shown in SEQ ID NO: 8 (NT4X-83); or
(b) a variable region comprising an amino acid sequence which is at least 80%, preferably 85%, more preferably 90%, even more preferably 95%, most preferably 97%, such as 100% identical to the amino acid sequence as shown in SEQ ID NO: 15, and comprising an amino acid sequence which is at least 80% identical to the amino acid sequence as shown in SEQ ID NO: 16 (NT4X-167); or
(c) a variable region comprising an amino acid sequence which is at least 80%, preferably 85%, more preferably 90%, even more preferably 95%, most preferably 97%, such as 100% identical to the amino acid sequence as shown in SEQ ID NO: 7 (VH NT4X-83); or
(d) a variable region comprising an amino acid sequence which is at least 80%, preferably 85%, more preferably 90%, even more preferably 95%, most preferably 97%, such as 100% identical to the amino acid sequence as shown in SEQ ID NO: 15 (VH NT4X-167); or
(e) a variable region comprising an amino acid sequence which is at least 80%, preferably 85%, more preferably 90%, even more preferably 95%, most preferably 97%, such as 100% identical to the amino acid sequence as shown in SEQ ID NO: 8 (VL NT4X-83); or
(f) a variable region comprising an amino acid sequence which is at least 80%, preferably 85%, more preferably 90%, even more preferably 95%, most preferably 97%, such as 100% identical to the amino acid sequence as shown in SEQ ID NO: 16 (VL NT4X-167).

Preferably, said antibody molecule is selected from a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a polyvalent antibody-construct, a synthetic antibody, a cross-cloned antibody, a fully-human antibody, a humanized antibody, nanobodies, and diabodies, polyvalent nanobodies or diabodies.

In a related aspect, the present invention also relates to a nucleic acid molecule encoding the antibody molecule according to the invention. Preferably, the nucleic acid molecule comprises the antibody molecule encoding sequence in functional linkage with additional regulatory sequences, which direct the expression and translation of the coding sequence. Examples for regulatory sequences are a promoter, e.g. a regulatory promoter, an enhancer, a poly-A signal sequence, and a signal peptide encoding region. The choice of the regulatory sequences will highly depend on the host cell to be used for expression of the nucleic acid molecule. Alternatively, the nucleic acid molecule may not contain any further regulatory sequences.

The nucleic acid molecule may be comprised in a vector. Generally, a vector is any vehicle used to integrate foreign nucleic acid material into a cell or cell genome, and typically contains elements that are capable of introducing, maintaining, and/or expressing nucleic acid sequences into a cell or, integrating nucleic acid sequences into the genome of a cell or of a host organism. Preferably, a suitable vector according to the invention further comprises an element selected from the group consisting of an origin of replication, a selectable marker, a transposon, a polytropic transposon, a retrovirus, an element capable of homologous recombination, and an element capable of non-homologous recombination. Generally, a wide variety of suitable vectors are known in the art and available to the skilled person. Accordingly, the invention also relates to a host cell comprising the nucleic acid molecule or the vector described above. Generally, the host cell may be any suitable prokaryotic or eukaryotic cell which is susceptible for transformation or transfection with the nucleic acid molecule or vector described herein. For example, such host cell may be a bacterial cell, e.g. a cell of *E. coli* or *B. subtilis*, a yeast cell, e.g. a *Saccharomyces* cell, a fungal cell, e.g. an *Aspergillus* cell, or a eukaryotic cell, e.g. a mammalian cell, a rodent cell, e.g. a CHO cell, a human cell or an insect cell. An overview of examples of different corresponding expression systems to be used for generating the host cell, is described, for example, in Bitter et al. (Methods in Enzymology 153 (1987), 516-544), in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440), Colonna et al. (1992) J. Imm. Methods 152: 89-104, Gurtu et al. (1996) Biochem. Biophys. Res. Comm. 229: 295-298. The transformation or genetically engineering of the host cell with a nucleic acid molecule or vector can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

In particular, such a host cell is useful in producing the antibody molecule. In this context, the invention further provides a method of producing an antibody molecule according to the invention comprising the step of (i) culturing the host cell or the hybridoma of the invention under conditions allowing synthesis of said antibody molecule and (ii) recovering said antibody molecule from said culture. Culturing will depend on the host cell in question, and includes fermentation in small scale and in large scale in laboratory and industrial fermenters, under conditions which are conducive for the production of the antibody molecule. Usually culturing is performed in liquid media comprising, for example, a carbon source, a nitrogen source, trace minerals and metals, as well as growth factors. Suitable culture media are known in the art. If the antibody molecule is secreted into the culture medium, it can be directly isolated from the culture. Otherwise, it might become necessary to disrupt the cells first in order to release the antibody molecule from the periplasma or cell into the culture medium. Methods for recovering an antibody molecule from a culture are also known in the art and may include precipitation, chromatographic procedures, such as affinity chromatography (e.g. Protein A or Protein G chromatography), hydroxylapatit chromatography, hydrophobicity chromatography, ion exchange chromatography, size exclusion chromatography, and/or electrophoretic procedures. As apparent from the above, these purification steps may be combined, e.g. by first conducting a protein A chromatography and subsequently a hydroxylapatit chromatography. Depending on the purification conditions chosen, the antibody molecule may be separated in the fractions or in the flow through.

As discussed above, it is believed that the antibody molecule described herein is useful and may be used in medicine and veterinary medicine, i.e. it may be used in the manufacture of a medicament, e.g. a medicament for the treatment of Alzheimer's disease. Accordingly, the antibody molecule described herein may be used in the treatment and/or prevention of Alzheimer's disease, in particular wherein the Alzheimer's disease is sporadic Alzheimer's disease or familial Alzheimer's disease. In a preferred embodiment, the Alzheimer's disease is sporadic Alzheimer's disease. In another preferred embodiment, the Alzheimer's disease is familiar Alzheimer's disease, including those caused by mutations in APP (arctic and Swedish mutation) and Presenilin-1 (PS1).

For this purpose, the antibody molecule is preferably formulated in a pharmaceutical composition comprising a pharmaceutically acceptable carrier, excipient and/or diluent. The carrier may be chosen dependent on the route of administration as well as on the concentration of the antibody molecule. The pharmaceutical composition may be in the form to of a lyophilised composition or an aqueous solution, in particular a stabilized aqueous solution. Generally, an appropriate amount of a pharmaceutically acceptable salt is used in the carrier to render the composition isotonic. For example, the carrier may include but is not limited to phosphate buffered saline, Ringer's solution, dextrose solution, water, emulsions, such as oil/water emulsions, various types of wetting agents, sterile solutions, etc. The acceptable excipients, carriers, or stabilisers are non-toxic at the dosages and concentrations employed, including buffers such as citrate, phosphate, and other suitable organic acids; salt-forming counter-ions, e.g. sodium and potassium; low molecular weight (>10 amino acid residues) polypeptides; proteins, e.g. gelatine, or serum albumin; hydrophilic polymers, such as polyvinylpyrrolidone; amino acids, e.g. histidine, glutamine, lysine, asparagine, arginine, or glycine; carbohydrates including glucose, mannose, dextrins, mono- and/or disaccharides, e.g. sucrose, mannitol, trehalose or sorbitol; complexing agents, e.g. EDTA; non-ionic surfactants, such as Pluronics, Tween, or polyethylene glycol. Preservatives may also be present such as, for example, antimicrobials, anti-oxidants, chelating agents, and inert gases and the like. Examples for antioxidants and/or preservatives are, e.g. methionine, ascorbic acid, tocopherol, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, or m-cresol. Suitable carriers and their formulations are described in greater detail in Remington's Pharmaceutical Sciences, 17th ed., 1985, Mack Publishing Co.

Accordingly, in another aspect, the invention pertains to a method of treating or preventing Alzheimer's disease in a subject, comprising the step of administering an antibody molecule according to the invention to said subject.

The subject may be a non-human animal, preferably a mammal such as a horse, cow, pig, mouse, rat, guinea pig, cat, dog, goat, sheep, non-human primate, or a human. The subject may be a healthy subject, a subject having/suffering from Alzheimer's disease, or subjects showing/having susceptibility for the development of Alzheimer's disease (e.g. carrying a genomic mutation which correlates with the occurrence of Alzheimer's disease, such as Swedish mutation, arctic mutation, etc.). Thus, in one preferred embodiment, the Alzheimer's disease is sporadic Alzheimer's disease. In another preferred embodiment, the Alzheimer's disease is familial Alzheimer's disease. Preferably, the antibody molecule is formulated in a pharmaceutical composition comprising a pharmaceutically acceptable carrier, to excipient and/or diluent, as defined above.

In one embodiment, the pharmaceutical composition may comprise the antibody molecule in an amount of about 10 ng/kg to about 5 mg/kg or about 10 mg/kg, and the pharmaceutical composition may be administered at a suitable dose, i.e. about 1 ng/kg body weight to about 100 mg/kg body weight of a subject, preferably at a dose of about 10 ng/kg to about 10 mg/kg, more preferably at a dose of about 10 ng/kg to about 5 mg/kg per body weight. However, the dosage regimen will be determined by an attending physician and depend upon many factors, including the patient's size and condition, body surface area, age, sex, time and route of administration, and on other drugs being administered concurrently. Administration will preferably be intravenously but may also be subcutaneously, intramuscularly, intraperitoneally, intracranially or directly into the cerebral fluid or selected brain regions. The compositions comprising an antibody molecule as described and provided herein may also be administered directly, e.g., by biolistic delivery to an internal or external target site or by catheter to a site in an artery or a vein.

The antibody molecule, preferably formulated in a pharmaceutical composition, may be administered, e.g., enterally, orally (e.g., formulated as a pill, tablet (buccal, sublingual, orally, disintegrating, capsule, thin film, liquid solution or suspension, powder, solid crystals or liquid), rectally (e.g., as a suppository, enema), via injection (e.g., intravenously, subcutaneously, intramuscularly, intraperitoneally, intradermally) via inhalation (e.g., intrabronchially), topically, vaginally, epicutaneously, or intranasally. Preferably, the composition is administered via injection, in particular intravenously, subcutaneously, intramuscularly, intraperitoneally, or intradermally; more preferably the composition is administered intravenously. It is also contemplated to administer the antibody molecule or the pharmaceutical composition directly into cerebral fluid or selected brain regions, i.e. intracranially.

Preparations for parenteral administration include sterile aqueous solutions, e.g., water, alcoholic/aqueous solutions, including saline and buffered media, including include sodium chloride solution, Ringer's dextrose, dextrose and sodium chloride solution, lactated Ringer's solution; or non-aqueous solutions, e.g., propylene glycol, polyethylene glycol, vegetable oils (such as olive oil), and injectable organic esters (such as ethyl oleate), suspensions, and emulsions. Intravenous vehicles include fluid and nutrient replenishers, electrolyte replenishers (such as those based on Ringer's dextrose), and the like.

However, the antibody molecule disclosed herein may also be formulated and comprised in a diagnostic composition. In this case, the antibody molecule may be linked with a marker or label, such as a dye, e.g. a fluorescence dye, a marker enzyme, or a compound which is detectable in routine diagnostic methods and medical scanning procedures. Accordingly, the diagnostic composition may be formulated for in vivo or in vitro use.

Hence, also contemplated is the use of an antibody molecule in accordance with the invention in a method of diagnosing Alzheimer's disease, and a method of diagnosing Alzheimer's disease, comprising the step of determining the amount of low molecular weight oligomers, in particular trimeric and tetrameric oligomers of Aβ in a sample of a subject to be diagnosed, using an antibody molecule according to the invention. The sample may be a blood sample, a cerebrospinal fluid sample, a serum sample, or a brain tissue sample. In a preferred embodiment, the step of determining the amount of low molecular weight oligomers of Aβ is conducted by means of an ELISA, e.g. as described above. Alternatively, the step of determining the amount of low molecular weight oligomers of Aβ is conducted by means of immunohistochemistry.

The antibody molecule, e.g. as formulated in a diagnostic composition, may also be used in a method of identifying agents useful in the treatment and/or prevention of Alzheimer's disease, in particular wherein the Alzheimer's disease is sporadic Alzheimer's disease or familial Alzheimer's disease. For example, the antibody molecule may be used as a positive control, or to detect the amount of trimeric or tetrameric Aβ in a immunohistochemistry sample, as described above, in for example a test animal treated with the candidate agent. Accordingly, the antibody molecule disclosed herein may also be used in a method of monitoring the efficacy of a treatment of Alzheimer's disease, in particular wherein the Alzheimer's disease is sporadic Alzheimer's disease or familial Alzheimer's disease.

Thus, also provided is a method of monitoring the efficacy of a treatment of Alzheimer's disease, comprising the step of determining the amount of low molecular weight oligomers of Aβ in a sample of a subject to be diagnosed using an antibody molecule as disclosed herein. Similar to the method of diagnosing Alzheimer's disease, the step of determining the amount of low molecular weight oligomers of Aβ may be conducted by means of an ELISA; and the method may be conducted on a blood sample, a cerebrospinal fluid sample, a serum sample, or a brain tissue sample, as outlined above.

In the following, the present invention is illustrated by reference to figures, sequences and examples which are not intended to limit the scope of the present invention.

Immunostaining with IC16 showing abundant intraneuronal (small arrow) and plaque (large arrow) Aβ in the hippocampal formation (subiculum) at 1.5 months of age using IC16 (A) and to a lesser amount using NT4X-167 (B). Blood vessel staining (cerebral amyloid angiopathy, CAA) with IC16 (C) and NT4X-167 (D). Abundant intraneuronal Aβ staining at 1.5 months of age in sub-corctical region with IC16 (E) and NT4X-167 (F). Scale bars: A-D: 50 μm and E-F: 100 μm.

Figure 12:
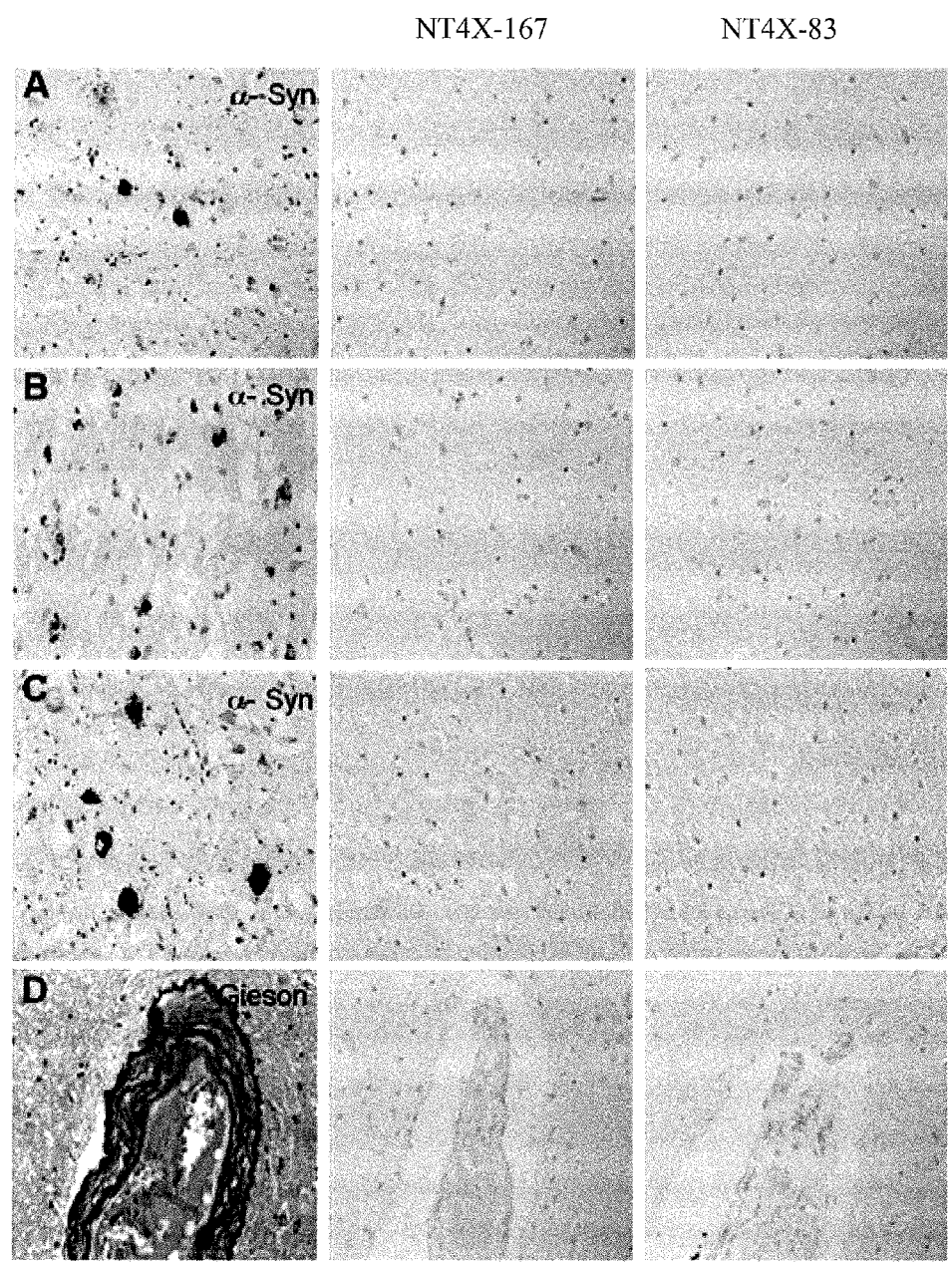
Figure 12:
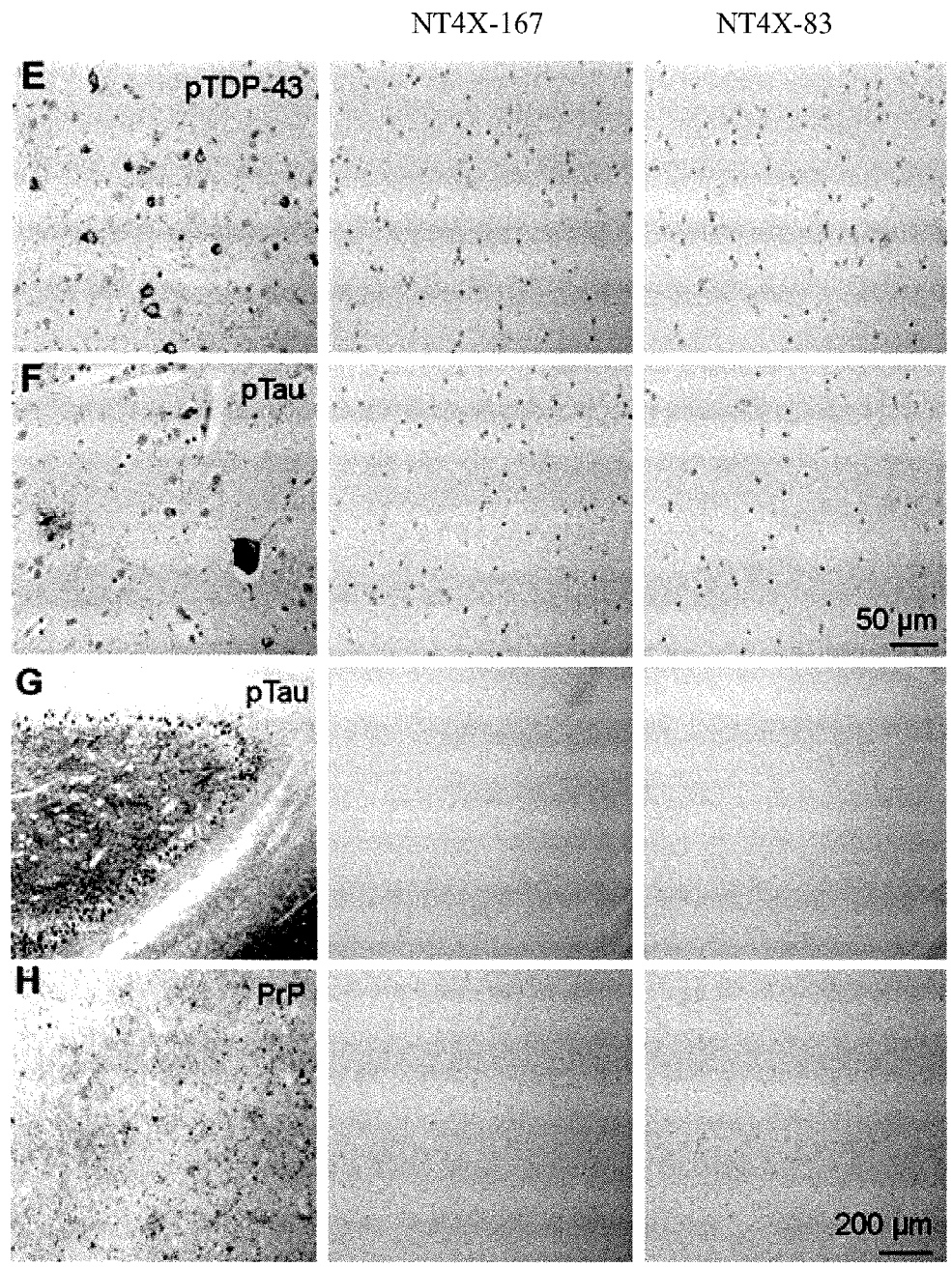

FIG. 12 No cross-reactivity of NTX4 antibodies with other aggregates of major neurodegenerative diseases. Alpha-synuclein (α-syn) positive aggregates in (A) Lewy bodies and Lewy neurites in Dementia with Lewy bodies (DLBD) and (B) Parkinson disease (PD) and (C) glial inclusions in Multiple system atrophy (MSA). (D) Pathological vessels in Binswanger encephalopathy. (E) Phospho-TDP-43 immunoreactive neuronal cytoplasmic in a case with Frontotemporal lobar degeneration (FTLD). Phospho-Tau (pTau) immunoreactive aggregates in (F) Progressive supranuclear palsy (PSP) and (G) in Pick's disease (PiD). (H) Prion protein (PrP) immunopositive synaptic deposits in sporadic Creutzfeldt-Jakob disease (CJD). Scale bar in A-F 50 μm, G-H, 200 μm.

Figure 13:
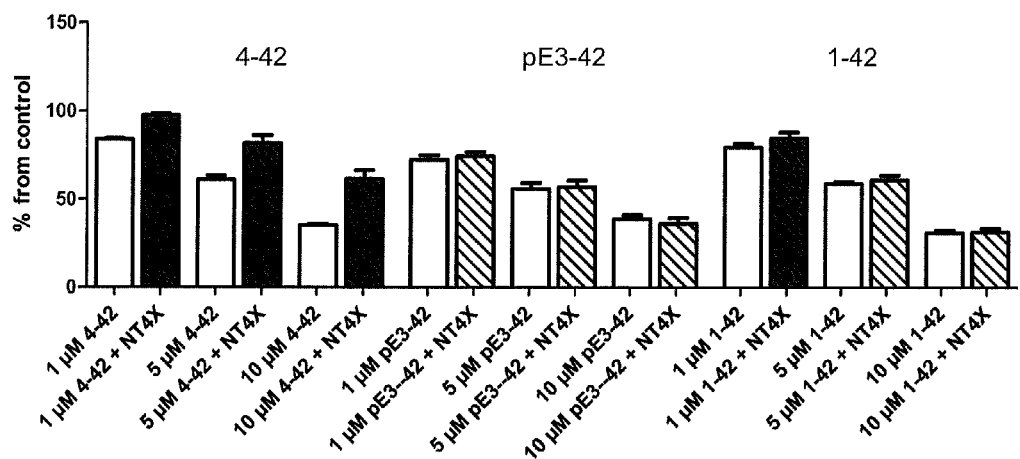

FIG. 13 NT4X treatment rescued toxic effect of freshly dissolved Aβ$_{4-42}$ but not of pyroglutamate AβpE$_{3-42}$ and only weakly of Aβ$_{1-42}$ in vitro. In rat primary cortical neurons, all Aβ peptides induced significant cellular toxicity compared to cultures without peptide. NT4X treatment rescued the toxic effects with high potency only of cultures treated with Aβ4-42. While NT4X treatment rescued toxicity of 1 μM of Aβ$_{1-42}$, 5 and 10 μM could not be rescued. The toxicity of AβDE$_{3-42}$ could not be rescued by NT4X at all concentrations tested.

Figure 14:
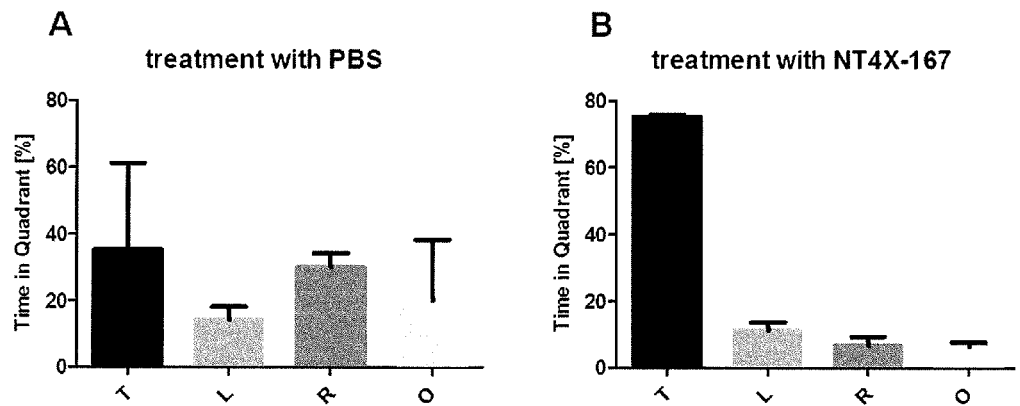

FIG. 14 Passive immunization with NT4X-167 antibody rescued memory deficits in aged 5XFAD mice. Twenty-four hours after the last acquisition trial, a probe trial was performed to assess spatial reference memory between placebo-treated (PBS) versus NT4X-167 immunized 5XFAD mice. A: At 30 weeks of age, PBS-treated 5XFAD mice displayed no significant preference for the target quadrant, as indicated by the percentage time spent in different quadrants of the pool. B: 5XFAD mice, which received intraperitoneal injections of 10 mg/kg NT4X-167 antibody starting at the age of 20 weeks (10 weekly injections between week 20 and 30) showed a significant preference for the target quadrant indicating that their spatial reference memory was restored. Abbreviations: T=target quadrant; L=left quadrant; R=right quadrant; O=opposite quadrant; m=age in months.

DESCRIPTION OF THE SEQUENCES

NT4X-83 HCDR1 (SEQ ID NO: 1):
GFNIRDTY

NT4X-83 HCDR2 (SEQ ID NO: 2):
VDPANGNT

NT4X-83 HCDR3 (SEQ ID NO: 3):
ARRIYYGYALFAY

NT4X-83 LCDR1 (SEQ ID NO: 4):
QSLLNSGNQKNY

NT4X-83 LCDR2 (SEQ ID NO: 5):
WAS

NT4X-83 LCDR3 (SEQ ID NO: 6):
QNDYSYPLTY

NT4X-83 VH (SEQ ID NO: 7):
EVHLQQSGAELVKPGASVKLSCTASGFNIRDTYIHWVKQRPEQGLEWI
GRVDPANGNTKYDPKFQGKATITADTSSDTAYLQLSSLTAEDTAVYFC
ARRIYYGYALFAYWGQGTLVTVSA

NT4X-83 VL /SEQ ID NO: 8):
DIVMTQSPSSLTVTAGEKVTMSCKSSQSLLNSGNQKNYLTWYQQKPGQ
PPKLLIYWASTRESGVPDRFTGSGSGTDFTLTISSVQAEDLAVYYCQN
DYSYPLTFGAGTKLELK

NT4X-167 HCDR1 (SEQ ID NO: 9):
GFSLTSYG

NT4X-167 HCDR2 (SEQ ID NO: 10):
MWSGGIT

NT4X-167 HCDR3 (SEQ ID NO: 11):
ARGSRYALDY

NT4X-167 LCDR1 (SEQ ID NO: 12):
QDISNY

NT4X-167 LCDR2 (SEQ ID NO: 13):
YTS

NT4X-167 LCDR3 (SEQ ID NO: 14):
QQGNTLPPT

NT4X-167 VH (SEQ ID NO: 15):
QVQLKQSGPGLVQPSQSLSITCTVSGFSLTSYGIHWVRQSPGKGLEWL
GVMWSGGITDFYAAFISRLSISRDISKSQVFFKMNSLQADDTAIYYCA
RGSRYALDYWGQGTSVSVSS

NT4X-167 VL (SEQ ID NO: 16):
DIQMTQTTSSLSASLGDRVTISCRASQDISNYLNWYQQKPDGTVKLLI
YYTSRLHSGVPSRFSGSGSGTDYSLTISNLEQEDIATYFCQQGNTLPP
TFGGGTKLEIK

Human Aβ$_{1-42}$ (SEQ ID NO: 17):
DAEFRHDSGYEVHHQKLVFFAEDVGSNKGAIIGLMVGGVVIA

DEPOSITED BIOLOGICAL MATERIAL

The following samples have been deposited in accordance with the Budapest treaty on the international recognition of the deposits of microorganisms for the purposes of patent procedure at the DSMZ, German Collection of Microorganisms and Cell Cultures in Braunschweig, Germany:

| Reference given by the Depositor | Date of deposit | Accession number |
|---|---|---|
| NT4X-83 | 7 Mar. 2012 | DSM ACC3161 |
| NT4X-167 | 7 Mar. 2012 | DSM ACC3162 |

EXAMPLES

Statistical differences were evaluated using one-way ANOVA followed by Dunnett's multiple comparison test or unpaired t-test as indicated. All data are given as mean±standard error of the mean (SEM). All statistics were calculated using GraphPad Prism V5.00 software (USA).

Example 1

Generation and Screening of Antibodies specific for Aβ$_{1-42}$ Trimerstetramers The novel oligomeric Aβ specific antibodies NT4X-83 (IgG2a; official name of cell line Aβ$_{4-40}$ NT4X-83; DSM ACC3161) and NT4X-167 (IgG1; official name of cell line Aβ$_{4-40}$ NT4X-167; DSM ACC3162) were generated by immunizing three Balb/c mice with unconjugated Aβ$_{4-40}$. After preparation of the lymph nodes they were fused with the myeloma cell line P3-X63-Ag8 for generation of the hybridoma cells. The hybridoma supernatants of mixed clones were screened by ELISA and subcloned.

The monoclonal antibodies were selected by enzyme-linked immune-absorbent assay (ELISA) and immunohistochemistry. The idea behind the generation of novel oligomeric antibodies was that Aβ$_{4-40}$ peptides are forming dimers in solution that can be used as a stable epitope for antibodies that bind specifically at the N-terminus of Aβ$_{4-40}$. Therefore Aβ$_{4-40}$ was used for immunizing mice and positive clones screened in four steps. After fusion, the hybridoma cells were screened by an ELISA for antibody production that (1) bind Aβ$_{4-10}$ and (2) Aβ$_{4-40}$, but (3) not Aβ$_{36-40}$. Positive antibody clones were further screened by immuno-histochemical staining of human brain sections. (4) The last step of the screening procedure was that they should not preferentially bind to amyloid plaques. Two monoclonal antibodies were identified NT4X-83 and NT4X-167 and further characterized.

Example 2

Epitope Mapping of NT4X-83 and NT4X-167

Figure 1:
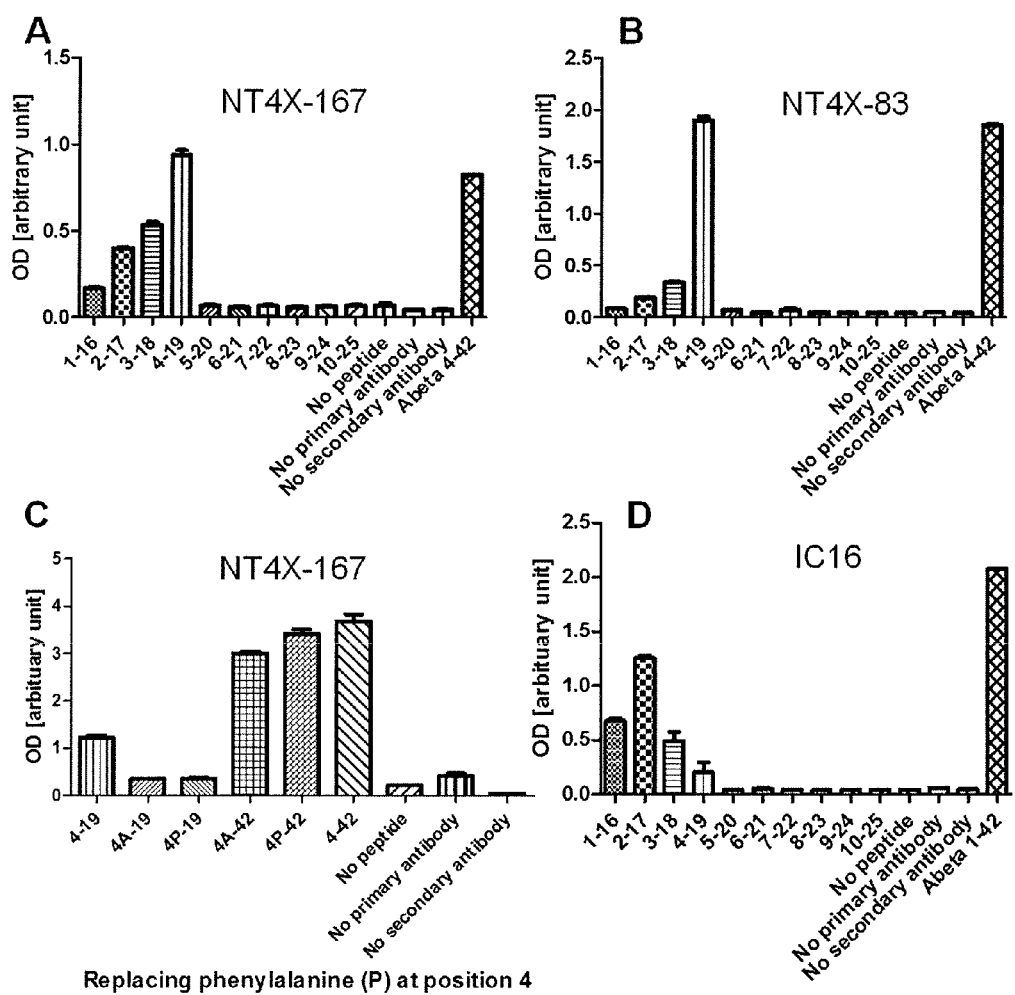
FIG. 1 Pepscan analysis using ELISA of (A, C) NT4X-167 and (B) NT4X-83 as well as IC16 (D) antibodies. Linear peptides with 16 amino acids in length were probed and incubated with NT4X antibody. NT4X-67 recognized amino acid position 1-4 with phenylalanin at position 4 with the highest intensity. No signals above background were seen with no peptide, no primary nor secondary antibody. As expected the positive control $A\beta_{4-42}$ reacted with the antibody. (C) NT4X-167 signal was completely abolished by replacing phenylalanine with alanine (A) or proline (P).

Pepscan assays (FIG. 1) were performed in order to identify the epitope binding of NT4X-167 and NT4X-83 as well as IC16. Pepscan is a procedure for mapping and characterizing epitopes involving the synthesis of overlapping peptides and analysis of the peptides in enzyme-linked immunosorbent assay (ELISAs). Aβ peptides with 16 amino acids in length were used: Aβ$_{1-16, 2-17, 3-18, 4-19, 5-20, 6-21, 7-22, 8-23, 9-24}$ and $_{10-25}$. The experiment was performed using U form high binding 96 well-plate (microplates, Greiner bio-one) to coat the peptides. Samples were diluted in ice cold sterile-filtered 0.05 M carbonate buffer (2.4 g NaCO$_3$×10 H$_2$O, 1.46 g NaHCO$_3$ added to 450 ml ddH$_2$O, pH 9.6) and 50 µl of the diluted samples were coated on the wells (the well-plate was kept on ice for some min before peptide application). For the peptide binding, the well-plate was incubated overnight at 4° C. The next day, the wells were washed three times by 0.01 M PBS (RT). The washing was done by applying 250 µl PBS into each well and emptying it by inverting the plate and hit it hard on a spongy cloth.

After the washing step, three other steps were followed (each step for 1 h at 25° C.):
Blocking (preventing unspecific antibody binding).
Incubation with primary antibody ((NT4-X (167) 1:300, 7 µg/ml, NT4-X (83) 1:100, 7 µg/ml and IC16 1:750).

Incubation with the secondary antibody (I-1RP coupled goat anti-mouse IgG, Dianova, 1:10.000, cat no: 115-035-003).

After each mentioned step, three times washing with 0.01 M PBS was applied.

For the blocking step, 200 µl of the RT blocking solution containing 5% w/v Albumin Fraction V (Roth) in 0.01 M PBS, which was prepared, sterile filtered and kept at 4° C. a day before the use was used.

Both, primary and secondary antibodies, were diluted in the blocking solution and 100 µl of each dilution was used for each well.

Lastly, as a HRP enzyme substrate, 50 µl of 3,3',5,5'-Tetramethylbenzidin (1-step Ultra TMB ELISA substrate, Thermo Scientific), that leads to the blue color production when oxidized, was added to each of the wells and the absorbance (OD) was measures within 5-10 min at 652 nm by a microplate reader (pQuant, BTek Instrument INC) using Mikro Win 2000 software (Berthold Technologies). The reaction was stopped by adding 50 µl of 2 M, $H_3PO_4$ which led to the yellow color formation and the absorbance was measured at 450 nm.

Using pepscan ELISA for signal detection, revealed that the binding site of NT4X-167 and NT4X-83 ranged between N-truncated $A\beta_{2-4}$ with the highest signal for N-truncated $A\beta_4$ starting with phenylalanine at position four. No major difference in the binding specificity between both NT4X antibodies was detected. Mutational analysis of $A\beta_{4-19}$ replacing phenylalanine with alanine ($A\beta_{4A-19}$) or proline ($A\beta_{4P-19}$) inhibited binding of NT4X-167 antibody. Therefore phenylalanine at position four of Aβ appears to be essentially required for antibody binding. IC16 reacted with aminoacids 1-4 and is therefore specific for the N-terminus of Aβ.

Example 3

Binding Characteristics of NT4X-83 and NT4X-167

For Western blot analysis under reducing conditions, peptides were loaded on 4-12% SDS VarioGels Tris-Tricin (Anamed; cat. no#VG41210), transferred to 0.45 µm nitrocellulose membranes and detected using the primary antibodies IC16 (1 µg/ml) and NT4X (7 µg/ml). Stock solutions of synthetic Aβ peptides (1 mg/ml in 10 mM NaOH) were prepared, sonicated for 5 min in water bath, quickly frozen in liquid nitrogen and stored at −80° C. Using 7 µg of freshly dissolved peptides from stock solutions NT4X-167 recognized LMW oligonneres of $A\beta_{1-42}$, $A\beta_{pE3-42}$ and $A\beta_{4-42}$ as well as monomers and dimers of $A\beta_{pE3-42}$, $A\beta_{4-42}$, $A\beta^{4-38}$ and $A\beta_{4-40}$. It did not recognize monomers and dimers of $A\beta_{1-42}$ (exposure time 10 seconds).

For the experiments, desired amount of the purred synthetic full length Aβ peptides were mixed with loading buffer (VarGel SDS Probenpuffer, Anamed) in the ratio of 1:1 and the peptides were denatured for 5-10 min at 95° C. (Uno-Thermoblock, Biometra). The denatured proteins were loaded on 4-12% Tris-Tricin gels with 1 mm of thickness. 5 µl of Spectra™ Multicolor low and broad range protein ladders (Thermo and Fermentas) were also loaded on different wells. The proteins were run by VarGel Tricin Running buffer (Anamed) and separated due to electrophoresis starting with 60 V for 15-20 min and continuing with 150 V for about 1 h. After the completion of running, proteins were transferred from the gel to 0.45 µm nitrocellulose membrane (GE Healthcare). For transferring the proteins, semi-dry method (BRAD, Trans-Blot® SD Semi-Dry) was used, as followed:

The membrane, gel and also two thick blotting papers were wetted into the transfer buffer. Wet thick papers were placed around the membrane and the gel (the membrane was lying under the gel) and the protein transfer was performed at 25 V for 40 min (Trans-Blot®SD semi-dry Transfer cell, BIO-RAD).

Upon the completion of protein transferring, the membrane was washed two times each for 10 min in 1× TBS/T (0.1 M Tris, 1.5 M NaCl and 0.5% Tween 20) on a rotator (Heidolph, DOUMAX 1030) with speed of 40 rpm. For Aβ peptides, membranes were boiled in 0.1 M PBS for about 1 min in microwave (ShARP) on 800 Watt power. After the start of boiling, the power was decreased to 80 Watt and the boiling was continued for 4 more minutes. Membranes were briefly washed in 1× TBS/T and blocked with 10% non-fat dry milk (Roth) in 1× TBS/T for 1 h at room temperature (RT) (40 rpm shaking). The membrane was incubated with following primary antibodies overnight at 4° C. or 2 h at RT (40 rpm shaking). This step was followed by two times of washing with 1× TBS/T each for 10 min (40 rpm shaking) and the membrane was incubated with secondary antibody (Polyclonal goat anti-mouse, Dianova diluted 1:4000) conjugated with horseradish peroxidase, for 2 h at RT. After washing for two times, each for 10 min, for development, the membrane was incubated in the horseradish peroxidase substrate solution containing 8 ml solution A (0.25 mg/ml luminal (Roth) in 0.1 M Tris/HCl), 800 µl solution B (1.1 mg/ml para-coumaric (Roth) acid in DMSO (Sigma) and 2.5 µl $H_2O_2$ (Roth) for 2 min. After slightly drying the membrane on a tissue paper, it was exposed to x-ray films (Hyperfilm EC, Amersham Biosciences) for different time points and developed in a CUR1x60 (AGFA).

For Western blotting under native conditions 18% SDS-free Tris-Glycine Progels (Anamed) [TG18110] were used. NT4X-167 is more sensitive as 70 ng of AB peptides having similar signal intensity as 500 ng detected with NT4X-83. Using these conditions, no signal for $A\beta_{1-42}$, $A\beta_{4-38}$ and $A\beta_{4-40}$ was detected. Only LMW of $A\beta_{4-42}$ and $A\beta_{pE3-42}$.

In brief, the peptides were mixed with the dye (Tris-Glycin Native Probenpuffer, Anamed) in the ration of 1:1 for 5 min at RT. Then, the desirable amount of the protein and dye was loaded on the 18% SDS-free gels (Progel Tris Glycin 18%, 1.0 mm, Anamed). Running the proteins on the gel was done using the SDS-free running buffer (Tris-Glycin Native Laufpuffer Anamed). The same nitrocellulose membranes as SDS-reduced Western blotting were used to which the proteins were transferred and the difference in the transferring was the content of the transfer buffer used. In the latter method, instead of 20% methanol, 5% methanol was used. Transferring the proteins to the membrane was accomplished using 25 V for 1 h. All the not mentioned conditions were the same as SDS-reduced Western blotting.

Buffers Used:

SDS-reduced western blotting transfer buffer:
48 mM Tris-HCL buffer, 39 mM glycin (20% methanol) pH 9.2

Native western blotting transfer buffer:
48 mM Tris-HCL buffer, 39 mM glycin (5% methanol) pH 9.2

Monomerization of Aβ Peptides

Synthetic Aβ peptides (PSL, GmbH, Heidelberg) were dissolved in a final concentration of 1 mg/ml in 10 mM NaOH. Next, the dissolved peptides were sonicated for 5 min with the instrument frequency of 35 KHz and the maximum power of 160 W and frozen in liquid nitrogen and stored at −80° C. till until further use.

Aging of Aβ Peptides

Monomerized peptides (1 mg/ml in 10 mM NaOH) were incubated for 20 h in a 37° C. incubator with shaking (60 rpm). Thereafter, they were transferred to 4° C. and were incubated for 4 days (96 h) without shaking.

1. Preference of NT4X binding for Aβ tetramers under denaturing conditions

Figure 2:
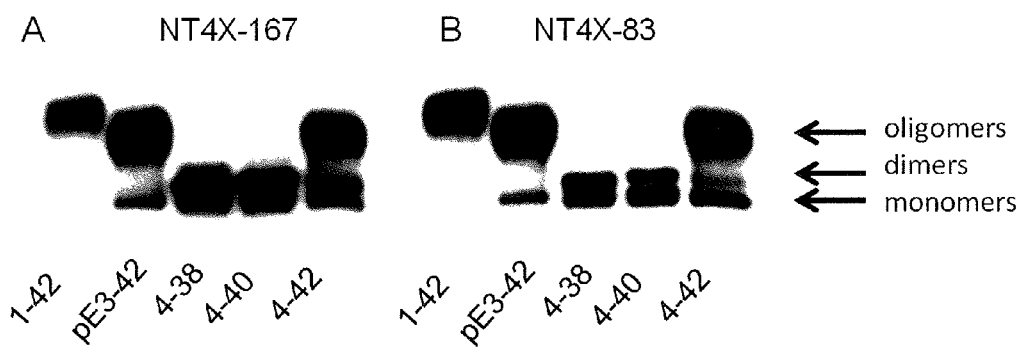
FIG. 2 SDS-PAGE Western blot analysis of NT4X antibodies. Freshly dissolved synthetic Abeta (7 μg) variants were probed to a membrane and incubated with (A) NT4X-167 and (B) NT4X-83 antibodies. The antibodies recognized low molecular weight tetrameric oligomeres of $A\beta_{1-42}$, $A\beta_{pE3-42}$ and $A\beta_{4-42}$ as well as monomers and dimers of $A\beta_{pE3-42}$, $A\beta_{4-42}$, $A\beta_{4-38}$ and $A\beta_{4-40}$. This experiment demonstrates that the NT4X antibodies have a preferential binding to low molecular weight oligomers of the most abundant $A\beta_{x-42}$ variants in the brain of AD patients, but lack binding to $A\beta_{1-42}$ monomers and dimers.

Freshly dissolved Aβ peptides were subjected to SDS-PAGE to dissect the binding specificity of NT4X antibodies (FIG. 2). Under denaturing conditions NT4X antibodies detected only low molecular weight (LMW) oligomers of $Aβ_{1-42}$ representing likely tetramers and no monomers or dimers. NT4X detected LMW oligomers derived from $Aβ_{pE3-42}$ and $Aβ_{4-42}$ with lower reactivity for monomers or dimers. NT4X antibodies detected only monomers and dimers of $Aβ_{4-38}$ and $Aβ_{4-40}$.

Figure 3:
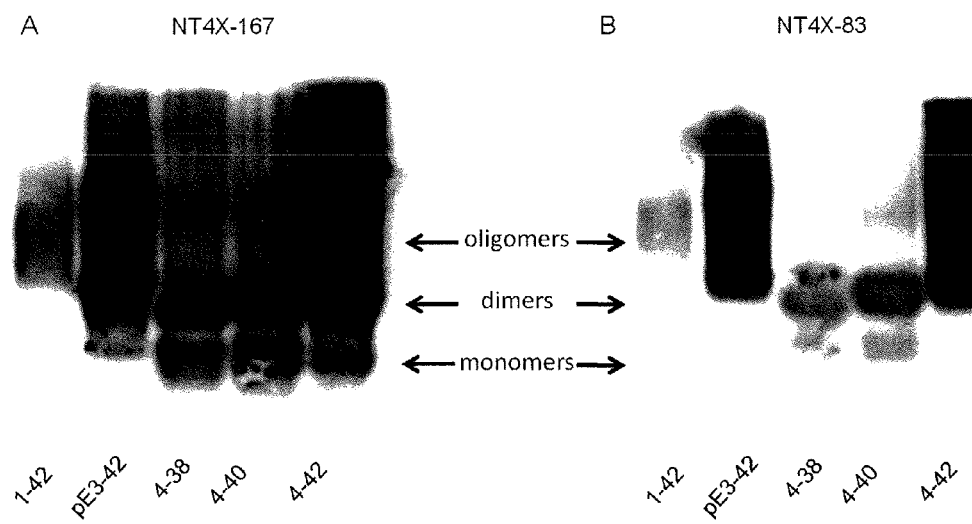
FIG. 3 Native Western blot of NT4X antibodies. Freshly dissolved Aβ (7 μg) variants were probed to a membrane and incubated with (A) NT4X-167 and (B) NT4X-83 antibodies. The antibodies recognized abundant LMW oligomeres of $A\beta_{1-42}$, $A\beta_{pE3-42}$ and $A\beta_{4-42}$ as well as monomers and dimers of $A\beta_{pE3-42}$, $A\beta_{4-42}$, $A\beta_{4-38}$ and $A\beta_{4-40}$. Of note, $A\beta_{1-42}$ monomers or dimers were not observed with NT4X antibodies. This experiment demonstrates that the NT4X antibodies have a preferential binding to LMW oligomers of the most abundant $A\beta_{x-42}$ variants in the brain of AD patients. There was no difference between NT4X-167 and NT4X-83 specificity.
Figure 5:
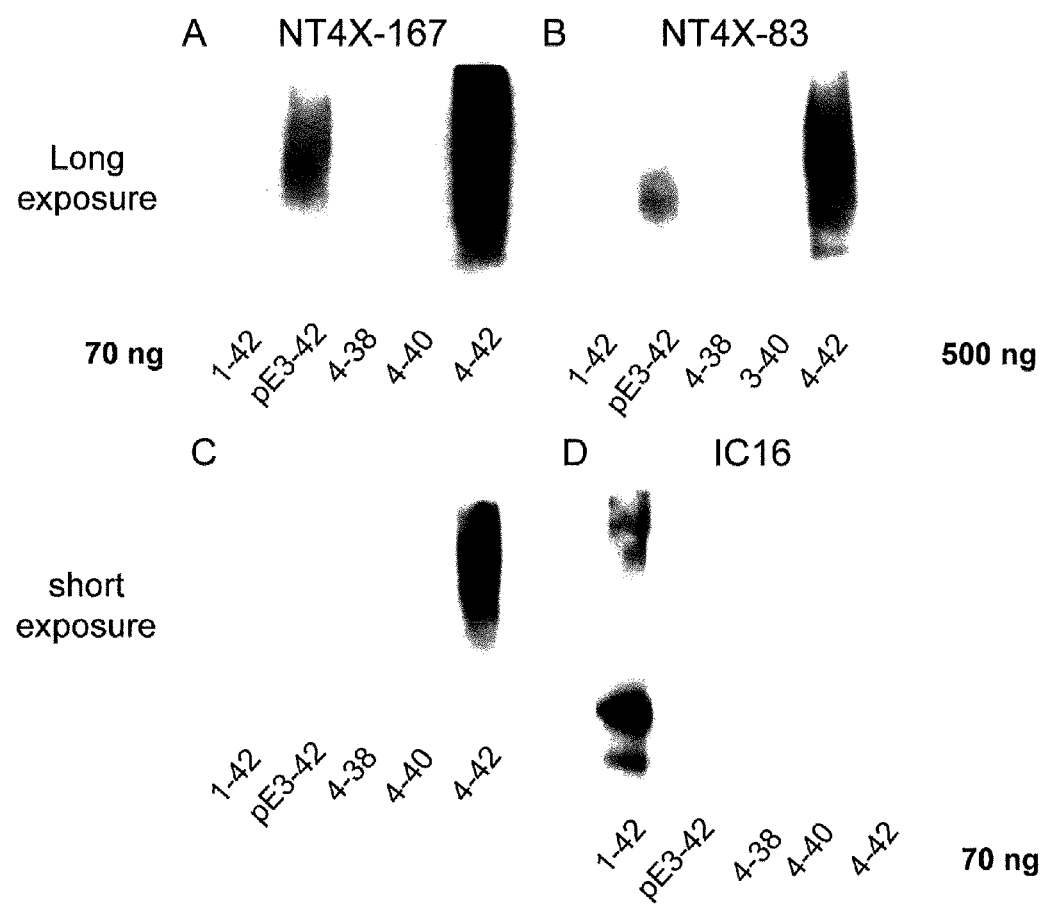
FIG. 5 Sensitivity of NT4X-167 using native Western blotting of freshly dissolved Aβ peptides. NT4X antibodies recognized Aβ$_{4-42}$ oligomers with the highest sensitivity followed by Aβ$_{pE3-42}$ in the μM range with (A) NT4X-167 being more sensitive as 70 ng of peptides having similar signal intensity as 500 ng detected with (B) NT4X-83. (C) represent a shorter exposure compared to A. (D) IC16 detected monomers and oligomers of full length 1-42, but none of the N-truncated peptides.

2. Preference of NT4X antibodies for Aβ low molecular weight oligomers under native conditions Under native conditions (FIG. 3), freshly dissolved Aβ peptides ending at amino acid 42 ($Aβ_{1-42}$, $Aβ_{pE3-42}$, $Aβ_{4-42}$) immediately formed oligomers, a tendency not observed for $Aβ_{4-38}$ and $Aβ_{4-40}$. As expected, the oligomers are running as less distinct bands under native conditions as compared to SDS PAGE. Although equal amounts of peptides were loaded, the strongest signal with NT4X antibodies were detected with oligomers of $Aβ_{4-42}$ followed by $Aβ_{pE3-42}$ and lastly by $Aβ_{1-42}$. NT4X detected only monomers and dimers of $Aβ_{4-40}$ and $Aβ_{4-38}$. The sensitivity for NT4X-167 to detect $Aβ_{4-42}$ and $Aβ_{pE3-42}$ was in the low μM range and was more sensitive compared to NT4X-83 (FIG. 5).

Figure 4:
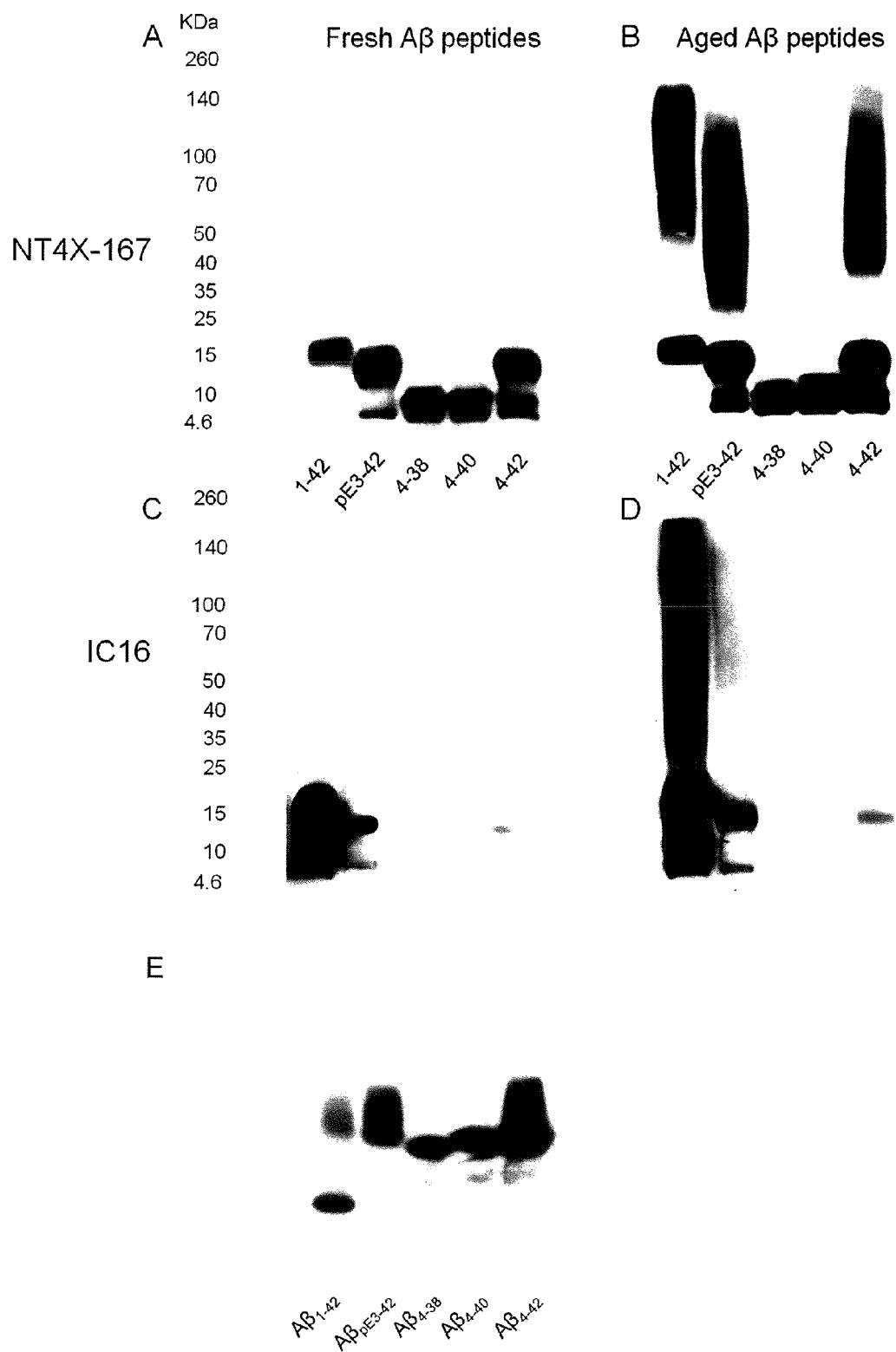
FIG. 4 Western blot of freshly dissolved comparing with aged Aβ peptides under reducing conditions. Aβ variants (7 μg) were probed to a membrane and incubated with NT4X-167 and IC16 antibodies. (A) Using freshly dissolved peptides NT4X-167 recognized low molecular weight (LMW) oligomeres of $A\beta_{1-42}$, $A\beta_{pE3-42}$ and $A\beta_{4-42}$ as well as monomers and dimers of $A\beta_{pE3-42}$, $A\beta_{4-42}$, $A\beta_{4-38}$ and $A\beta_{4-40}$. It did not recognize monomers and dimers of Aβ$_{1-42}$. (B) Using aged peptides NT4X-167 also recognized high molecular weight (HMW) oligomeres of Aβ$_{1-42}$, Aβ$_{pE3-42}$ and Aβ$_{4-42}$. (C) Using freshly dissolved peptides IC16 only recognized monomers, dimers and LMW oligomeres of Aβ$_{1-42}$, Aβ$_{pE3-42}$ and Aβ$_{4-42}$. Of note, IC16 strongly reacted with Aβ$_{1-42}$ aggregates followed by Aβ$_{pE3-42}$. (D) Aged peptides showed the same profile with a much stronger reactivity of HMW oligomers of Aβ$_{1-42}$, which was weaker for Aβ$_{pE3-42}$. (E) Under native conditions freshly dissolved AR peptides displayed formation of abundant oligomers of different sizes. Aβ$_{1-42}$ run mostly as low molecular weight oligomers, while the N-truncated Aβ peptides displayed prominent bands a higher molecular weight. Native Western blot of Aβ peptides using the pan-Aβ polyclonal antiserum 24311.

3. Aging of Aβ induced SDS-resistant high molecular weight oligomers detected by NT4X A comparison of SDS-PAGE Western blot of freshly dissolved peptides with aged Aβ peptides (20 h at 37° C. with gentle shaking followed by 96 h at 4° C.) (FIG. 4) demonstrated that NT4X-167 reacted with high molecular weight (HMW) oligomers of $Aβ_{1-42}$, $Aβ_{pE-42}$ and $Aβ_{4-42}$, In contrast, IC16 only reacted with $Aβ_{1-42}$ HMW oligomers. $Aβ_{4-38}$ and $Aβ_{4-40}$ did not generate HMW oligomers under reducing condition. These findings argue for a unique and selective binding of NT4X to a conformational epitope formed by aged HMW $Aβ_{pE-42}$ and $Aβ_{pE-42}$ oligomers, which is not detectable by IC16 having its epitope between $Aβ_{1-3}$. Interestingly, HMW oligomers of $Aβ_{1-42}$ are also detected by NT4X.

Haass and Selkoe argued that small molecules that can specifically inhibit the formation of Aβ oligomers and/or prevent their binding to and stabilization on neuronal membranes is at the top of the pathological cascade in AD and will also be beneficial for down-stream events like tangle formation, synaptic and neuron loss and eventually cognitive decline (Haass and Selkoe (2007) *Nat Rev Mol Cell Biol* 8, 101-112). More recently, the group around De Strooper (Benilova et al. (2012) *Nat Neurosci advance online publication*) discussed that it is likely that several of the identified oligomeric species (mostly derived from $Aβ_{1-42}$) have similar or overlapping properties. Moreover, they state that coexistence of several o populations that do or do not propagate into fibrils is possible. Despite the differences in structure, stability and concentration, all oligomers may contribute to Aβ toxicity. They further discussed some technical issues defining oligomers like the apparent 'SDS resistance' (Benilova et al.; supra). It was demonstrated that SDS can induce artificially oligomerization of Aβ. Monomers, trimers and tetramers as major bands derived from Aβ oligomers, Aβ fibrils and Aβ monomers were isolated after SDS-PAGE separation.

Therefore other techniques like applying native Western blotting is a useful way characterizing Aβ oligomers. In the present report, we observed a striking difference between the binding of NT4X with Aβ peptides under reducing and native conditions. While under reducing conditions, LMW oligomers of $Aβ_{1-42}$, $Aβ_{pE3-42}$ and $Aβ_{4-42}$ were detected, a strong signal was seen for monomers of $Aβ_{pE3-42}$ and $Aβ_{4-42}$, but not $Aβ_{1-42}$. Under reducing conditions, $Aβ_{1-42}$, $Aβ_{pE3-42}$ and $Aβ_{4-42}$ formed stable LMW oligomers after dissolving the peptides. Aging of the peptides resulted in a shift of the SDS-stable signal $Aβ_{1-42}$, $Aβ_{pE3-42}$ and AB to HMW $Aβ_{4-42}$ to HMW oligomers. No difference was observed between under reducing and native conditions for $Aβ_{4-38}$ and $Aβ_{4-40}$, which apparently only formed monomers and dimers.

Example 4

Functional Characteristics of NT4X-83 and NT4X-167

Monomerization of synthetic peptides: Stock solutions of synthetic peptides (1 mg/ml in 10 mM NaOH; PSL, Heidelberg) were prepared, sonicated for 5 min in water bath (Sonorex RK 100H, Bandelin electronic), quickly frozen in liquid nitrogen and stored at −80° C.

Aging of peptides: Aged Aβ peptides were generated by incubation for 20 h at 37° C. with gentle agitation (60 r/min) followed by 96 h at 4° C. without shaking.

1. Antibody NT4X inhibited Aβ aggregation in vitro

Figure 6:
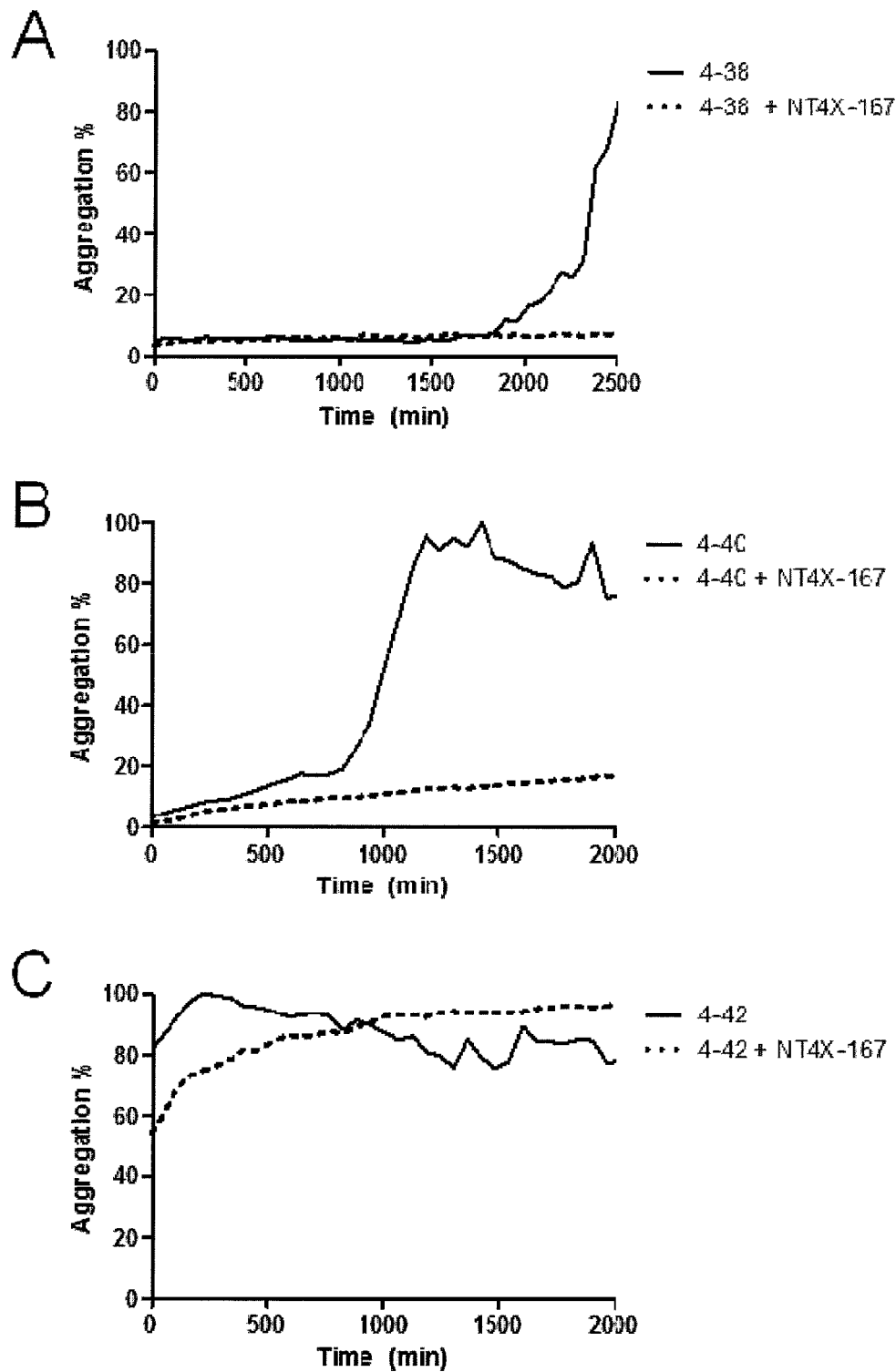
FIG. 6 Aggregation of Aβ peptides using ThT fluorescence assay. All Aβ peptides exhibited a typical aggregation profile. Co-incubation with NT4X-167 inhibited further aggregation: It clearly inhibited aggregation of (A) Aβ$_{4-38}$, (B) Aβ$_{4-40}$ (D) Aβ$_{1-42}$ and (E) Aβ$_{pE3-42}$. (C) The elevated aggregation signal of Aβ$_{4-42}$ at the beginning of the experiment indicates a poor level of monomers. Incubation with NT4X-167 lowered the aggregation signal demonstrating an inhibitory effect of the antibody treatment.
Figure 6:
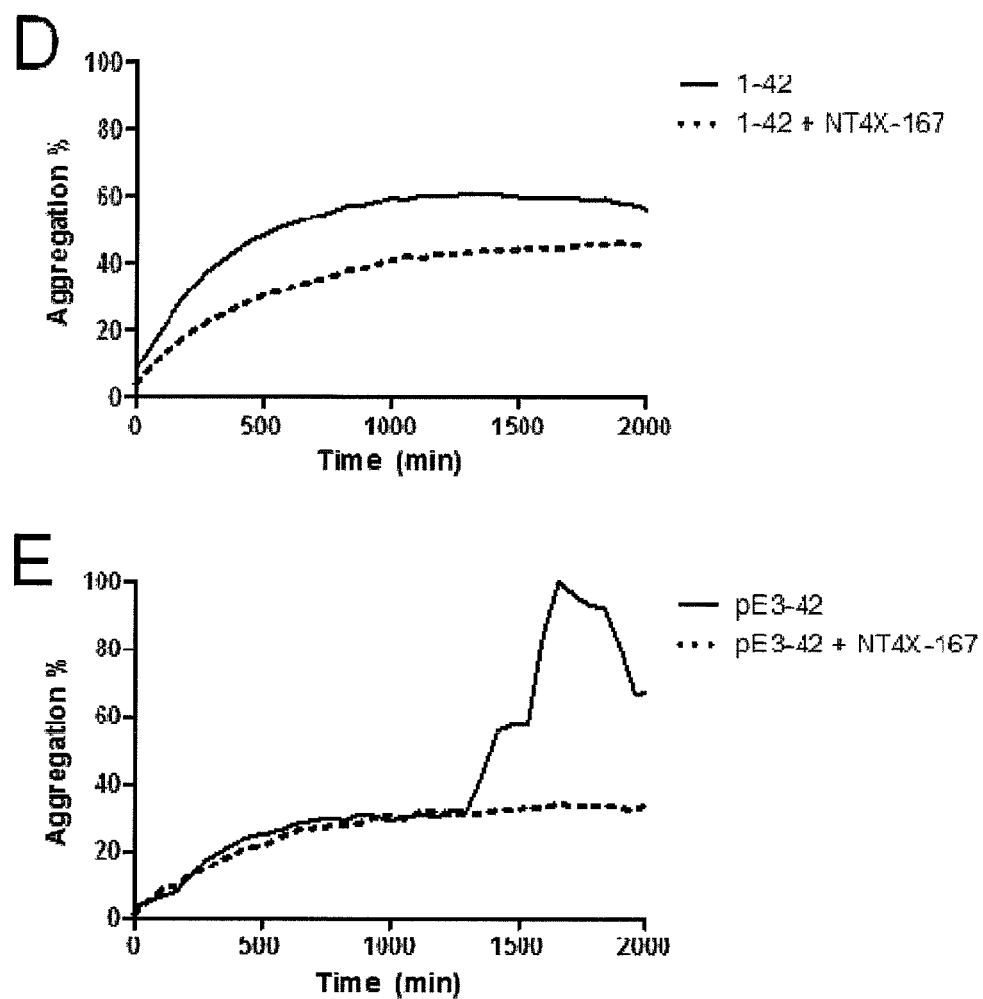

Aggregation of Aβ peptides was investigated online using ThT aggregation assay (Varian fluorescence spectrophotometer) using an excitation wavelength of 446 nm and emission wavelength of 482 nm. Samples contained 10 μM of Aβ, 50 mM sodium phosphate buffer (pH 7.4), 50 mM NaCl, 20 μM ThT and 0.01% sodium azide. The samples were incubated at 37° C. in a peltier adapter with stirring. Data points were recorded every 10 min during the assay. As shown in FIG. 6, all peptides aggregated over time. However, the aggregation of $Aβ_{4-38}$ started significantly later. Of note, the aggregation rate of $Aβ_{4-42}$ differed from all other peptides as they already started aggregation from a higher level. Notably, co-incubation with antibody NT4X-167 efficiently inhibited and or delayed the aggregation of all Aβ peptides (ratio of 5:1; antibody:Aβ). This observation argues for a beneficial treatment effect of both NT4X antibodies as they did not show any differences in recognition pattern.

2. Antibody NT4X rescued Aβ-induced cell toxicity

Figure 7:
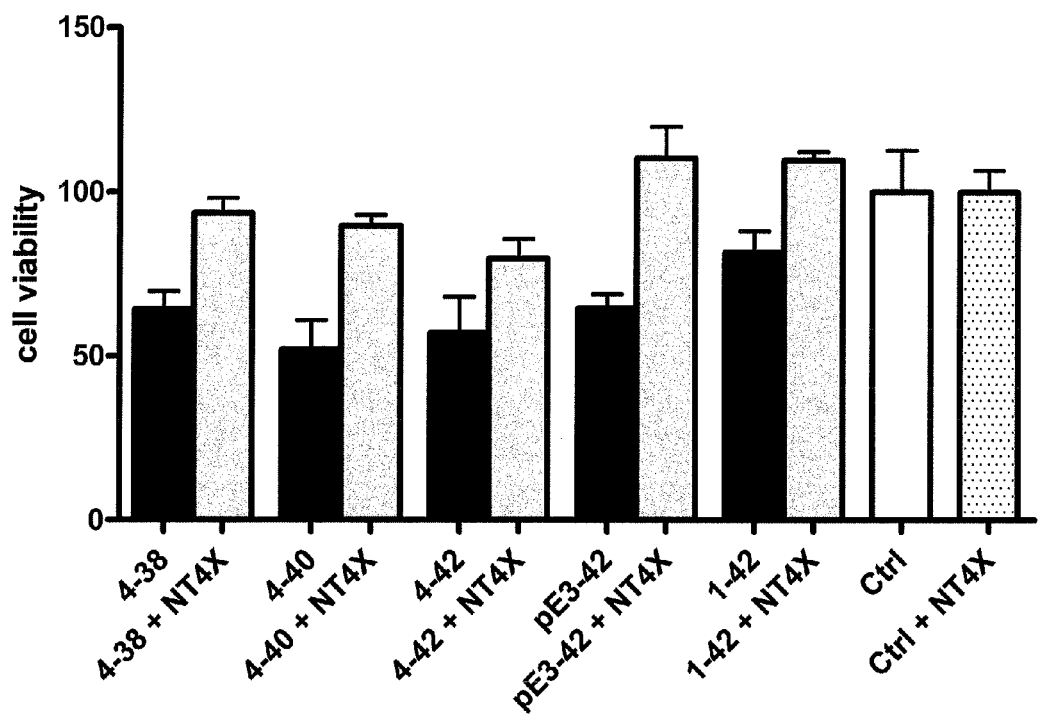
FIG. 7 Viability assay using SY5Y neuroblastoma cells. NT4X-167 antibody treatment rescued cell viability of neuroblastoma cells SY5Y. The monomerized 10 μM peptides were freshly dissolved and incubated together with the antibody for 20 h at 37° C., followed by incubation for 96 h at 4° C. without shaking. Aged peptides with or without antibody were applied to SY5Y cells for 12 h and the viability was measured by MTS. One-way analysis of variance demonstrated a significant difference within the groups of p<0.0001 (F=6.418, df=11) followed by Dunnett's multiple comparison test between the groups. The cell viability was significantly reduced by all peptides compared to untreated control cells (P<0.01) and was rescued by NT4X-167 treatment in all cases.

Next, the toxicity of aged Aβ peptides on SH-SY5Y neuroblastoma cells was studied (FIG. 7). To determine whether the toxic effect of Aβ can be neutralized by NT4X-167 antibody, neuroblastoma cells were co-incubated either with peptides alone or with peptides plus NT4X-167: SH-SY5Y neuroblastoma cells were routinely cultured. 5500 cells were cultured in the wells containing 200 μl of fresh pre-warm DMEM-F12 (PANT™ BIOTECH GmbH) medium for 24 h (at 37° C., 5% $CO_2$) and thereafter the cells were starved for 24 h using serum-free pre-warmed medium. After 24 h, medium was replaced by medium containing aged peptides in the presence or absence of NT4X-167 antibody and incubated for 24 h. Cell viability was determined using MTS assay (Promega), according to the manufacturer's instructions compared to vehicle treated control cells. The percentage of cell viability was calculated using the following formula: [($A_{490}$ sample–$A_{490}$ background)/($A_{490}$ control–$A_{490}$ background)]×100.

Using the aged peptide protocol a significant effect on cell viability with all Aβ peptides was observed with the N-truncated peptides having the strongest effect compared to Aβ$_{1-42}$. Dunnett's multiple comparison test gave the following significant results for the toxicity of 10 μM aged Aβ peptides: control versus Aβ$_{4-38}$ (p<0.05); control versus Aβ$_{4-40}$ (p<0.01);

control versus Aβ$_{4-42}$ (p<0.01); control versus Aβ$_{pE3-42}$ (p<0.05). Therapeutic effect of NT4X-167 was demonstrated by increased cell viability comparing application of Aβ versus Aβ and antibody: Aβ$_{4-38}$ (p<0.01); Aβ$_{4-40}$ (p<0.01); Aβ$_{4-42}$ (p<0.01); Aβ$_{pE3-42}$ (p<0.05); Aβ$_{1-42}$ (p<0.01). This observation argues again for a beneficial treatment effect of both NT4X antibodies as they did not show any differences in recognition pattern.

In view of the above data, the antibodies of the invention are believed to be highly valuable in a therapeutic treatment of AD.

Example 5

Diagnostic Properties of NT4X-83 and NT4X-167

Human and mouse tissue was processed as described previously (Wirths et al. (2010) *J. Neural Transm.* 117, 85-96). In brief, 4 μm paraffin sections were pretreated with 30% H$_2$O$_2$ in PBS to block endogenous peroxidases and antigen retrieval was achieved by boiling sections in 0.01 M citrate buffer pH 6.0, followed by 3 min incubation in 88% formic acid. Primary antibodies were incubated overnight, followed by incubation with biotinylated secondary antibodies (DAKO) before staining was visualized using the ABC method with Vectastain kit (Vector Laboratories) and diaminobenzidine as chromogen.

In brief, 4 μm brain sections were obtained by cutting paraffin-embedded brain tissue using a microtome. Deparaffinization was performed by incubation in xylol (Carl Roth GmbH) two times each for 5 min and followed by series of decreasing ethanol (Chemie-vertrieb) concentration (100%, 95% and 70% for 10, 5 and 3 min respectively) to rehydrate the sections. This stage was followed by 1 min washing the sections with deionized H$_2$O. Endogenous peroxidase blocking was achieved by incubation of the sections for 30 min in the solution of 200 ml 0.01 M PBS and 2 ml 30% H$_2$O$_2$. Sections were washed by deionized H$_2$O for 1 min. The antigen retrieval was performed by boiling the sections in 10 M Citrate buffer (4.2 g Citric acid-Monohydrate added to 2000 ml H$_2$O; pH=6) for 2 min in a microwave at 800 Watt power. After 2 min the power was decreased to 80 Watt and the boiling was continued for 8 more min. After cooling down the sections for 15 min they were washed with deionized H$_2$O for 1 min followed by incubation in 0.01 M PBS+0.1% Triton for 15 min and for 1 min incubation in 0.01 M PBS as washing step. Incubation with freshly prepared 88% formic acid for 3 min followed. Sections were washed twice by 0.01 M PBS for 1 and 5 min. Unspecific blocking was done by 1 h in 4% milk powder (Roth), 10% fetal cow serum (FCS) in 0.01 M PBS in wet a chamber at RT. Primary antibodies, diluted in 0.01 M PBS and 10% FCS, were applied on the sections and were incubated at RT overnight (in a wet chamber). On the next day, sections were washed three times, each for 5 min by 0.01 M PBS+0.1% Triton and for 1 min by 0.01 PBS. Then, secondary antibody (Rabbit anti-mouse, Dako, cat. no. E0354), conjugated with biotin was diluted 1:200 in 0.01 PBS and 10% FCS and was applied on the sections in the wet chamber and incubated for 1 h at 37° C. This step was followed by Avidin-Biotin complex (ABC) (Vectastain® Elite ABC Kit, Vector Laboratories; cat. No. PK6100) incubation at 37° C. for 1.5 h which was prepared and kept at 4° C. at least 30 min before its application. ABC solution was prepared as followed: 0.01 M PBS+10% FCS+1:100 solution A +1:100 solution B. Afterwards, three times washing with 0.01 PBS each time for 5 min, was done and the sections were exposed to diaminobenzidine (DAB) solution (5 ml 50 mM Tris/HCl PH 7.5+100 μl DAB stock solution (25 mg/ml 5-(4-Dimethylamino-Benzylidene)Rhodanine (sigma) in 0.05 M Tris/HCL, PH 7.4)+2.5 μl 30% H$_2$O$_2$ (Roth) (added right before use) for a few minutes until staining was observed. The sections were washed with 0.01 PBS, three times each time for 5 min, counterstaining was performed using filtered hematoxylin, for 40 s. The sections were dipped into deionized H$_2$O and then washed in running tap water for 5 min. As the last step in staining, sections were dehydrated by series of increasing ethanol concentration (1 min 70%, 5 min 95% and 10 min 100%) and in the end two times in xylol, each for 5 min. The sections, then, were embedded using eukitt quick hardening mounting medium (Carl Roth GmbH (Roti®-Histokit)).

Figure 8:
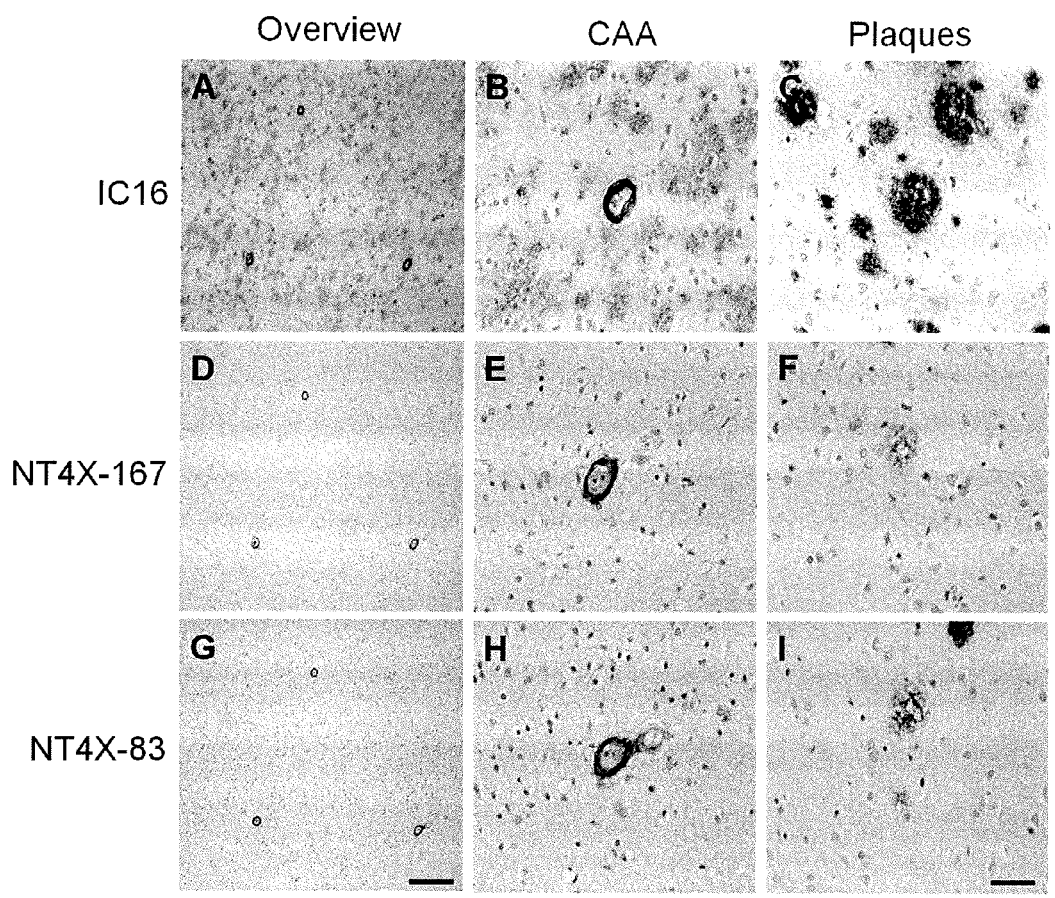
FIG. 8 Immunohistochemical staining pattern in superior temporalis gyrus of sporadic AD brain. Upper row shows the staining pattern in a sporadic AD case using IC16 antibody demonstrating different magnifications of cerebral amyloid angiopathy (CAA) and plaques (A-C). Second and the third row show the staining pattern of the same region as IC 16 using two novel antibodies, NT4X-167 and NT4X-83, respectively (D-F) and (G-I). Comparison of figure A with D and G clearly shows that occasionally NT4X-83 and -167 can recognize CAA rather than plaques even when abundant plaques are recognized by IC16. Both NT4X antibodies show a comparable staining pattern. Scale bar: A, D, G: 200 μm and B, C, E, F, H, I: 50 μm.
Figure 9:
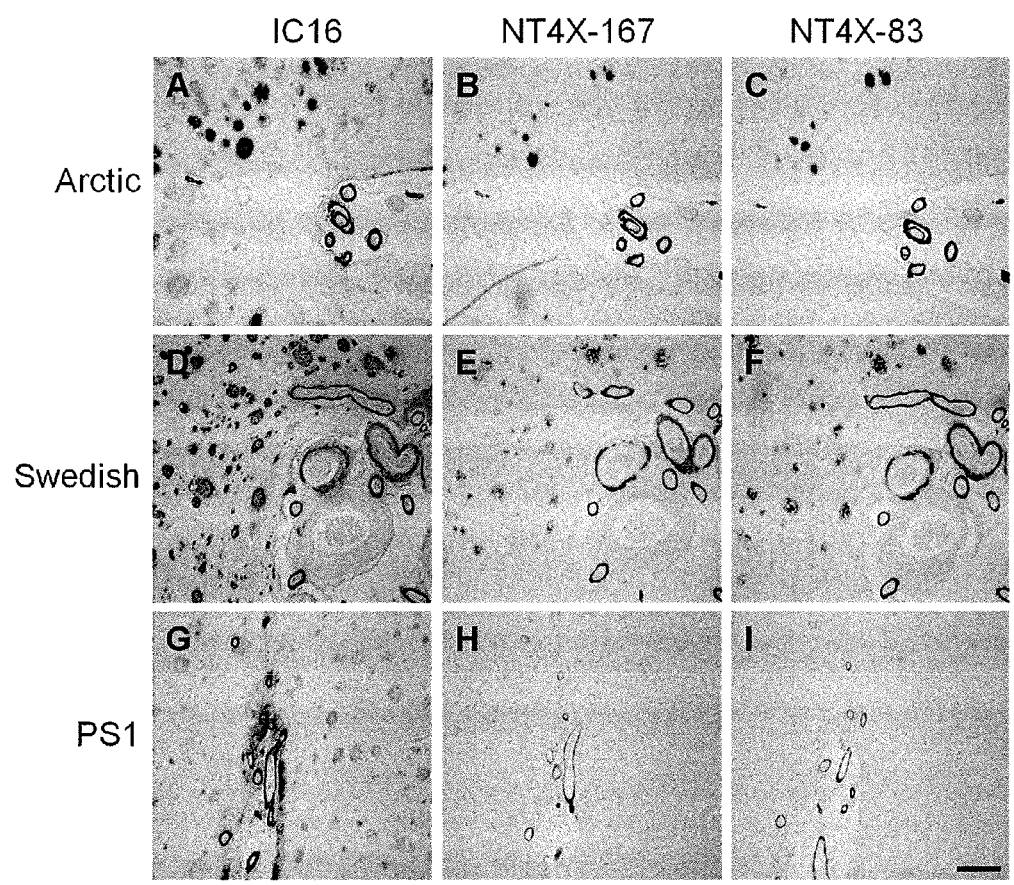
FIG. 9 Immunohistochemistry staining of cases with familial AD. Panel A-C and D-F illustrate brain sections from patients with an Arctic and Swedish mutation in the APP gene respectively. Panel 3 shows brain sections from a patient with a PS1 mutation with (G-I). While, shown in all the figures, much CAA is recognized by the tested antibodies (IC16, NT4X-167 and NT4X-83), plaques can be recognized by NT4X only in the APP Arctic and Swedish cases but not in the PS1 Familial AD case. Scale bar: 200 μm.

In order to characterize the staining pattern of the two NT4X antibodies in AD patients, cortical tissue sections with sporadic (Table 1, FIG. 8) and familial AD (Table 2, FIG. 9) were analyzed. Human brain samples were obtained from the Netherlands Brain Bank (NBB) and the Department of Pathology, University of Helsinki, Finland (a generous gift of Dr. Hannu Kalimo) and were approved by the local Ethical Committees. Compared to the IC16, both NT4X antibodies recognized only a minor portion of plaques in brain tissue of AD patients. Cerebral amyloid angiopathy (CAA) staining of blood vessel walls was seen with all antibodies. In familial AD cases, the amount of NT4X-positive plaques was almost absent in patients with a mutation in presenilin-1 gene (PS1), and much weaker in cases with an APP mutation compared to IC16 staining.

Table 1 lists the demographic data of sporadic AD patients and non-demented controls and the staining profile of the antibodies. Of note, none of the controls showed NT4X staining of plaques although 3 of them were positive with IC16 demonstrating a clear differentiation between AD and control cases. The amount of NT4X-positive plaques in sporadic AD brain was low. Abbreviations: No, number of cases; M, male; F, female; ApoE4, number of cases with at least one ApoE4 allele; CM, cerebral amyloid angiopathy

|  | No | Age Mean ± SEM | Sex M/F | Braak stage | ApoE4 | Plaques (IC16) | CAA (IC16) | Plaques (NT4X) | CAA (NT4X) |
|---|---|---|---|---|---|---|---|---|---|
| Sporadic AD | 13 | 76 ± 3 | 3/10 | 4-6 | 7/13 | 13/13 | 13/13 | 3/13 | 13/13 |
| Controls | 10 | 80 ± 2 | 6/4 | 0-1 | 2/10 | 5/10 | 3/10 | 0/10 | 3/10 |

Table 2 lists the demographic data and staining profile of the antibodies in familial AD cases. NT4X did not show any plaques in PS1 cases, while CM and plaques were observable in cases with Arctic and Swedish mutations in the APP gene. Abbreviations: M, male; F, female; CM, cerebral amyloid angiopathy.

| Gene | Mutation | Sex | Age | IC 16 Plaques | IC 16 CAA | NT 4-X Plaques | NT 4-X CAA |
|---|---|---|---|---|---|---|---|
| APP | Arctic | M | 64 | + | + | + | + |
|  | Swedish | F | 61 | + | + | + | + |
| PS1 | Δ Exon 9 | M | 61 | + | + | − | + |
|  |  | M | 64 | + | + | − | + |
|  |  | M | 69 | + | + | − | + |

Figure 10:
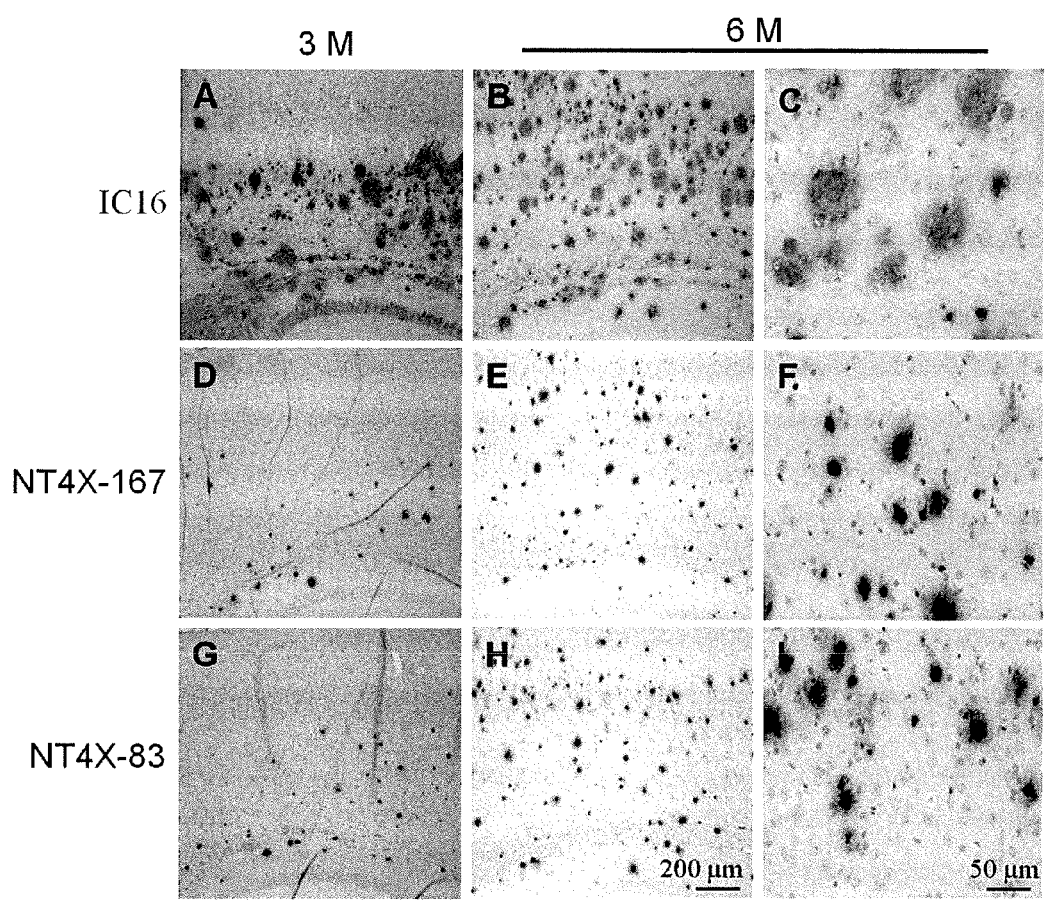
FIG. 10 Immunohistochemical staining of cortical sections of 3 and 6 months old 5XFAD transgenic mice. (A-C) Immunostaining with IC16 demonstrating age-dependent increase in plaque load. (D-F) Immunostaining with NT4X-167 showing age-dependent increase in plaque load however the amount of positives plaques was less pronounced compared to IC16. (G-I) The pattern for NT4X-83 was similar to NT4X-167. Scale bar: A, B, D, E, G and H: 200 μM and in image C, F and I: 50 μM.
Figure 11:
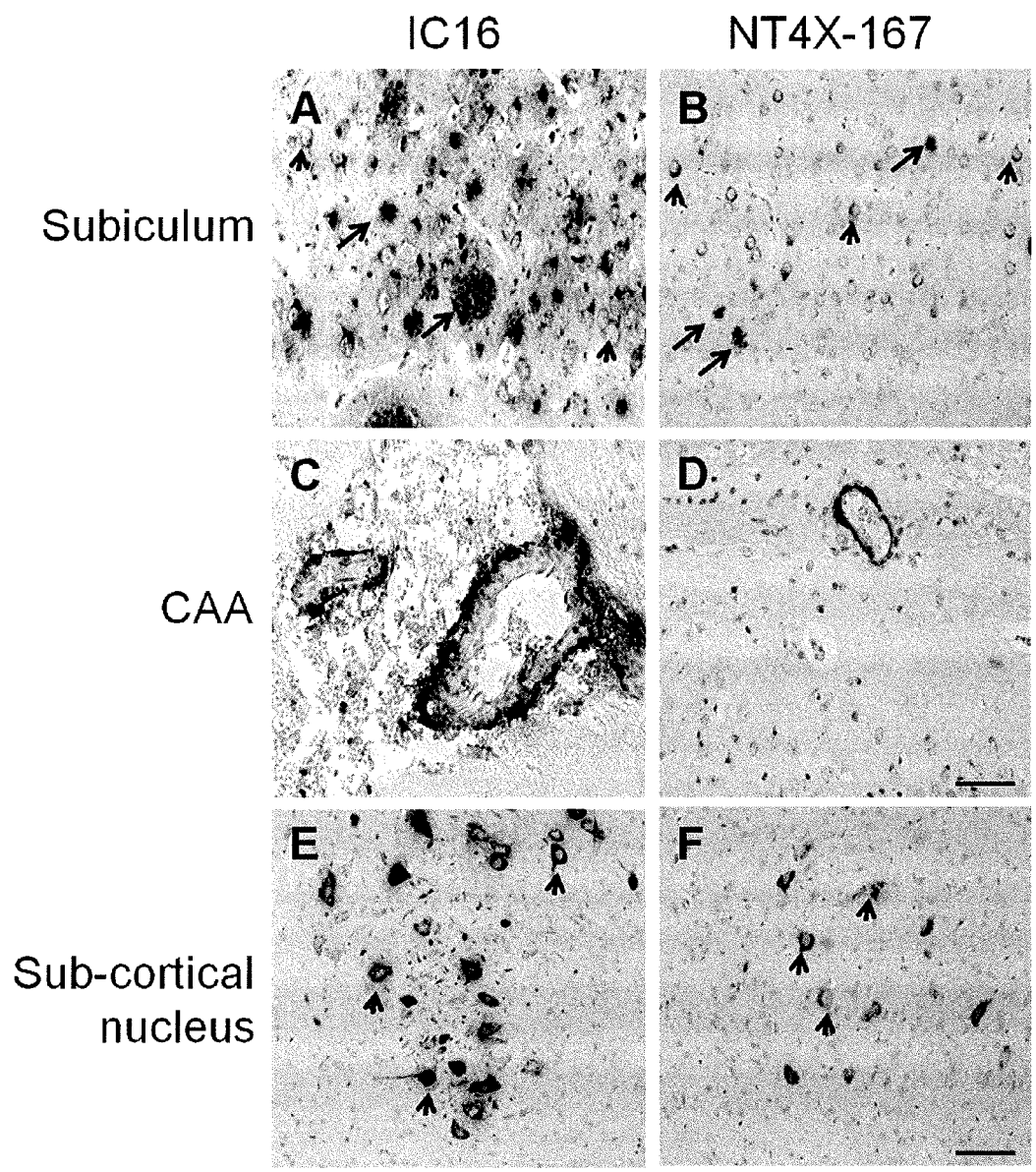
FIG. 11 Immunohistochemical staining of APP/PS1KI transgenic mouse brain. (A-B)

Next, the staining pattern in two transgenic AD mouse models 5XFAD and APP/PS1KI was analyzed. APP/PS1KI and 5XFAD mice have been described previously (Casas et al. (2004) *Am. J. Pathol.* 165, 1289-1300; Jawhar et al. (2012) *Neurobiol. Aging* 33). All mice were backcrossed for more than 10 generations on a C57BL/6J genetic background and housed at a 12-h day/12-h night cycle with free access to food and water. All animals were handled according to German guidelines for animal care and studies were approved by the local legal authorities (LAVES). In 5XFAD, IC16 already detected abundant plaques at 3 months of age NT4X antibodies reacted only with a fraction and stained preferentially the central core of plaques (FIG. 10). In APP/PS1KI mice, a model with an earlier and more robust pathology compared to 5XFAD, NT4X detected early aggregates starting at 1.5 months of age preferentially within neurons in the hippocampal formation and subcortical areas, blood vessel walls and some plaques (FIG. 11). These findings argue that NT4X antibodies detect early pathological aggregates in like intraneuronal Aβ aggregation, which has been demonstrated to induce neuron loss in this model.

In order to study a potential cross-reactivity with other disease-typical aggregates, brain tissue sections were stained with disease-specific markers and compared with NT4X reactivity. NT4X antibodies did not cross-react with other aggregated deposits of non-AD neurodegenerative disorders. The following pathological structures showed no immunoreactivity (Table 3; FIG. 12): (i) Phospho-Tau immunoreactive structures, including tufted astrocytes (PSP) and Pick bodies in PiD. (ii) α-Synuclein immunopositive Lewy bodies (brainstem and cortex) and Lewy neurites in PD and DLB, and glial cytoplasmic inclusions in MSA. (iii) Phospho-TDP-43 immunoreactive neuronal cytoplasmic and neuritic deposits in FTLD-TDP, ALS, and AD with limbic TDP-43 deposits. (iv) PrP immunopositive amyloid plaques, synaptic, plaque-like, and perineuronal deposits. In addition, there was no immunoreactivity associated with small vessel disease in Binswanger disease.

TABLE 3

Demographic data and examined anatomical regions of the cases for cases other neurodegenerative disorders.

| No | Case/Disease | Age | Sex | Examined regions |
|---|---|---|---|---|
| 1 | DLBD | 81 | F | Temporal Cx |
| 2 | PD | 62 | M | Mesencephalon (SN) |
| 3 | MSA | 52 | M | Pons |
| 4 | PSP | 69 | M | Basal Ganglia |
| 5 | PiD | 70 | F | Hippocampus + Ent Cx + Temp Cx |
| 6 | FTLD | 62 | F | Hippocampus + Ent Cx + Temp Cx |
| 7 | CJD MV | 72 | F | Hippocampus + Ent Cx + Temp Cx + Cbll |
| 8 | Binswanger disease | 49 | F | Basal Ganglia |

Abbreviations: DLBD, dementia with Lewy bodies; PD, Parkinson's disease; MSA, multiple system atrophy; PSP, progressive supranuclear palsy; PiD, Pick's disease; FTLD, frontotemporal lobar degeneration; CJD, Creutzfeldt-Jakob disease; M, male; F, female; Ent Cx: entorhinal cortex; Temp Cx; temporal cortex, SN: substantia nigra, Cbll: cerebellum.

In view of the above data, it is believed that the antibodies according to the invention are highly valuable for diagnosing AD.

Example 6

NT4X-167 Rescues Aβ1-42 and Aβ4-42 Toxicity In Vitro

To determine whether the toxic effect of Aβ can be neutralized by NT4X-167 antibody, primary cell cultures were co-incubated either with peptides alone or with peptides plus NT4X-167.

Cortical neurons from embryonic day 16-17 Wistar rat fetuses were prepared as previously described (Pillot et al., 1999). In brief, dissociated cortical cells were plated at 50.000 cells/well in 48-well plates precoated with 1.5 mg/mL polyornithine (Sigma). Cells were cultured in a chemically defined Dulbecco's Modified Eagle's/F12 medium free of serum (Gibco) and supplemented with hormones, proteins and salts. Cultures were kept at 35° C. in a humidified 5% $CO_2$ atmosphere, and at 6-7 DIV, cortical population is determined to be at least 97% neurons. At 6 DIV, the medium was removed and cortical neurons were incubated for 24 h with vehicle or Ab oligomers at the indicated concentrations.

Following a 24-h incubation of primary cortical neurons with Aβ oligomers, cell viability and in vitro toxicity was determined using a calcein-AM assay (Invitrogen, Molecular Probes) (see also Youssef et al., 2008). Briefly, cells were washed twice with PBS and incubated protected from light for 30 min at room temperature in the presence of 2 mM calcein-AM solution prepared in PBS. Cells were then washed twice with PBS and incubated for 15 min at room temperature in PBS containing 1% Triton X-100 (v/v). The level of calcein fluorescence was monitored by fluorescence emission at 530 nm after exciting at 485 nm, using a Fluostar microplate reader (BMG-Labtechnologies, France).

NT4X treatment rescued toxic effect of freshly dissolved $Aβ_{4-42}$, but not of pyroglutamate $AβpE_{3-42}$ and only weakly of $Aβ_{1-42}$ in vitro (cf. FIG. 13). In rat primary cortical neurons, all Aβ peptides induced significant cellular toxicity compared to cultures without peptide. NT4X treatment rescued the toxic effects with high potency only of cultures treated with $Aβ_{4-42}$. While NT4X treatment rescued toxicity of 1 μM of $Aβ_{1-42}$, 5 and 10 μM could not be rescued. The toxicity of $AβpE_{3-42}$ could not be rescued by NT4X at all concentrations tested.

Example 7

Spatial Reference Memory by Morris Water Maze

Spatial reference memory in 5XFAD mice (Oakley et al., 2006) was evaluated using the Morris water maze (Morris, 1984). Thereby, mice learn to use spatial cues to locate a hidden, circular platform (10 cm) in a circular pool (110 cm diameter) filled with tap water. The water was made opaque by adding non-toxic white paint and maintained at 20° C. for the test duration. The pool was divided into four virtual quadrants that were defined based on their spatial relationship to the platform: left, right, opposite and target quadrant, which contains the goal platform. ANY-Maze video tracking software (Stoelting Co., Wood Dale, USA) was used to record escape latency, path length, swimming speed and quadrant preference. In order to test whether the groups differed regarding their memory for the former location of the platform in the probe trial, we calculated for each mouse a platform quadrant preference ratas follows: Time spent in Target Quadrant (time spent in Target Quadrant+Time spent in Opposite Quadrant). Preference ratios close to 1 indicate well, whereas ratios close to 0 indicate poor spatial memory.

Female 5XFAD mice were tested at the age of 30 weeks. Each individual mouse was tested at one age only using the cued trials followed by the acquisition training and finalized by the probe trial. After the probe trial the mice were sacrificed. Testing began with three days of cued training. For these trials the platform was marked with a triangular flag. Mice were introduced into the water at the edge of the pool facing the wall. They were then given one minute to find the submerged platform. Mice that failed to find the platform in 60 sec were gently guided to it. All mice were allowed to sit on the platform for 10 sec before being removed from the pool. To prevent hypothermia, all mice were kept in front of a heat lamp for 3 min before being returned to their home cage. Each mouse received four training trials per day with an average inter-trial interval of 15 min. Both the location of the platform and the position at which mice were introduced into the pool changed between trials.

Twenty-four hours after the last day of cued training, mice performed five days of acquisition training. For this part of testing, the flag was removed from the platform. In addition to the distal cues existing in the room proximal visual cues were attached to the outside of the pool. The platform location remained stationary for each mouse throughout training. At the start of every trial, mice were introduced into the pool from one of four predefined entry points. The order in which these entry points were used varied between training days (Vorhees and Williams, 2006). To avoid quadrant bias, the experimental cohorts were randomly split and trained to find one of two different platform locations. Trials were conducted as during the cued training phase.

Twenty-four hours after the last acquisition trial, a probe test was performed to assess spatial reference memory. The platform was removed from the pool, and mice were introduced into the water from a novel entry point. Mice were then allowed to swim freely for one minute while their swimming path was recorded.

Twenty-four hours after the last acquisition trial, a probe trial was performed to assess spatial reference memory between placebo-treated (PBS) versus NT4X-167 immunized 5XFAD mice. At 30 weeks of age, PBS-treated 5XFAD mice displayed no significant preference for the target quadrant, as indicated by the percentage time spent in different quadrants of the pool (cf. FIG. 14A). 5XFAD mice, which received intraperitoneal injections of 10 mg/kg NT4X-167 antibody starting at the age of 20 weeks (10 weekly injections between week 20 and 30) showed a significant preference for the target quadrant indicating that their spatial reference memory was restored (cf. FIG. 14B).

All references cited herein are incorporated by reference.

LIST OF REFERENCES

EP 2 210 901
EP 2 246 427
WO 2009056490
WO 2009065054
WO 2011151076
U.S. Pat. No. 4,816,567
U.S. Pat. No. 7,763,249
Benilova, I., Karran, E., and De Strooper, B. (2012) The toxic A[beta] oligomer and Alzheimer's disease: an emperor in need of clothes, *Nat Neurosci advance online publication*.
Billman-Jacobe (1996) *Current Opinion in Biotechnology* 7, 500-4.
Bitter et al. (1987) *Methods in Enzymology* 153, 516-544.
Buchhave, P., Minthon, L., Zetterberg, H., Wallin, A. K., Blennow, K., and Hansson, O. (2012) Cerebrospinal Fluid Levels of {beta}-Amyloid 1-42, but Not of Tau, Are Fully Changed Already 5 to 10 Years Before the Onset of Alzheimer's Dementia, *Arch Gen Psychiatry* 69, 98-106.
Casas, C., Sergeant, N., Itier, J. M., Blanchard, V., Wirths, O., van der Kolk, N., Vingtdeux, V., van de Steeg, E., Ret, G., Canton, T., Drobecq, H., Clark, A., Bonici, B., Delacourte, A., Benavides, J., Schmitz, C., Tremp, G., Bayer, T. A., Benoit, P., and Pradier, L. (2004) Massive CA1/2 Neuronal Loss with Intraneuronal and N-Terminal Truncated A{beta}42 Accumulation in a Novel Alzheimer's Transgenic Model, *Am. J. Pathol.* 165, 1289-1300.
Coloma et al. (1992) *J. Imm. Methods* 152, 89-104.
Fukumoto, H., Tokuda, T., Kasai, T., Ishigami, N., Hidaka, H., Kondo, M., Allsop, D., and Nakagawa, M. (2010) High-molecular-weight beta-amyloid oligomers are elevated in cerebrospinal fluid of Alzheimer's patients, *Faseb J* 24, 2716-2726.
Griffiths et al. (1997) *Methods in Molecular Biology* 75, 427-440.
Gurtu et al. (1996) *Biochem. Biophys. Res. Comm.* 229, 295-298.
Haass, C., and Selkoe, D. J. (2007) Soluble protein oligomers in neurodegeneration: lessons from the Alzheimer's amyloid [beta]-peptide, *Nat Rev Mol Cell Biol* 8, 101-112.
Hampel, H., Frank, R., Broich, K., Teipel, S. J., Katz, R. G., Hardy, J., Herholz, K., Bokde, A. L. W., Jessen, F., Hoessler, Y. C., Sanhai, W. R., Zetterberg, H., Woodcock, J., and Blennow, K. (2010) Biomarkers for Alzheimer's disease: academic, industry and regulatory perspectives, *Nat Rev Drug Discov* 9, 560-574.
Hockney (1994) *Trends in Biotechnology* 12, 456-463.
Jager, S., Leuchtenberger, S., Martin, A., Czirr, E., Wesselowski, J., Dieckmann, M., Waldron, E., Korth, C., Koo, E. H., Heneka, M., Weggen, S., and Pietrzik, C. U. (2009) alpha-secretase mediated conversion of the amyloid precursor protein derived membrane stub C99 to C83 limits Abeta generation, *J Neurochem* 111, 1369-1382.
Jawhar, S., Trawicka, A., Jenneckens, C., Bayer, T. A., and Wirths, O. (2012) Motor deficits, neuron loss, and reduced anxiety coinciding with axonal degeneration and intraneuronal Abeta aggregation in the 5XFAD mouse model of Alzheimer's disease, *Neurobiol. Aging* 33.

Kang, J., Lemaire, H. G., Unterbeck, A., Salbaum, J. M., Masters, C. L., Grzeschik, K. H., Multhaup, G., Beyreuther, K., and Mueller-Hill, B. (1987) The precursor of Alzheimer's disease amyloid A4 protein resembles a cell-surface receptor, *Nature* 325, 733-736.

Kayed, R., Head, E., Thompson, J. L., McIntire, T. M., Milton, S. C., Cotman, C. W., and Glabe, C. G. (2003) Common structure of soluble amyloid oligomers implies common mechanism of pathogenesis, *Science* 300, 486-489.

Kim, Y. S., Moss, J. A., Janda, K. D. (2004) Development of Conformation-specific Antibodies for Neutralization of β-Amyloid Oligomers, *Neurobiology of Aging* 25, S145.

Klyubin, I., Betts, V., Wetzel, A. T., Blennow, K., Zetterberg, H., Wallin, A., Lemere, C. A., Cullen, W. K., Peng, Y., Wisniewski, T., Selkoe, D. J., Anwyl, R., Walsh, D. M., and Rowan, M. J. (2008) Amyloid beta protein dimer-containing human CSF disrupts synaptic plasticity: prevention by systemic passive immunization, *J. Neurosci.* 28, 4231-4237.

Klyubin, I., Walsh, D. M., Lemere, C. A., Cullen, W. K., Shankar, G. M., Betts, V., Spooner, E. T., Jiang, L., Anwyl, R., Selkoe, D. J., and Rowan, M. J. (2005) Amyloid beta protein immunotherapy neutralizes Abeta oligomers that disrupt synaptic plasticity in vivo, *Nat Med* 11, 556-561.

Kohler, G. et al. (1975), *Nature* 256, 495.

*Methods in Yeast Genetics, A Laboratory Course Manual*, Cold Spring Harbor Laboratory Press, 1990.

Morris, R. (1984), Developments of a water-maze procedure for studying spatial learning in the rat. *J. Neurosci. Methods* 11, 47-60.

Oakley, H., Cole, S. L., Logan, S., Maus, E., Shao, P., Craft, J., Guillozet-Bongaarts, A., Ohno, M., Disterhoft, J., Van Eldik, L., Berry, R., Vassar, R. (2006), Intraneuronal beta-Amyloid Aggregates, Neurodegeneration, and Neuron Loss in Transgenic Mice with Five Familial Alzheimer's Disease Mutations: Potential Factors in Amyloid Plaque Formation. *J. Neurosci.* 26, 10129-10140.

Ono, K., Condron, M. M., and Teplow, D. B. (2009) Structureneurotoxicity relationships of amyloid β-protein oligomers, *Proc. Natl. Acad. Sci.* 106, 14745-14750.

Pillot T, et al, (1999) The Nonfibrillar Amyloid β-Peptide Induces Apoptotic Neuronal Cell Death. *J. Neurochem*, 73(4), 1626-1634.

Portelius, E., Bogdanovic, N., Gustaysson, M. K., Volkmann, I., Brinkmalm, G., Zetterberg, H., Winblad, B., and Blennow, K. (2010) Mass spectrometric characterization of brain amyloid beta isoform signatures in familial and sporadic Alzheimer's disease, *Acta Neuropathol* 120, 185-193.

Sambrook and Russell (2001), *Molecular Cloning: A Laboratory Manual*, CSH Press, Cold Spring Harbor, N.Y., USA;

Sawers et al. (1996) *Applied Microbiology and Biotechnology* 46, 1-9.

Tanzi, R. E., Gusella, J. F., Watkins, P. C., Bruns, G. A. P., St. George-Hyslop, P. H., Van Keuren, M. L., Patterson, D., Pagan, S., Kurnit, D. M., and Neve, R. L. (1987) The amyloid β protein gene: cDNA cloning, mRNA distribution, and genetic linkage near the Alzheimer's locus, *Science* 235, 880-884.

Vorhees, C. V., Williams, M. T. (2006), Morris water maze: procedures for assessing spatial and related forms of learning and memory. *Nat. Protoc.* 1, 848-858.

Walsh, D. M., Klyubin, I., Fadeeva, J. V., Cullen, W. K., Anwyl, R., Wolfe, M. S., Rowan, M. J., and Selkoe, D. J. (2002) Naturally secreted oligomers of amyloid beta protein potently inhibit hippocampal long-term potentiation in vivo, *Nature* 416, 535-539.

Walsh, D. M., Tseng, B. P., Rydel, R. E., Podlisny, M. B., and Selkoe, D. J. (2000) The oligomerization of amyloid beta-protein begins intracellularly in cells derived from human brain, *Biochemistry* 39, 10831-10839.

Wang, X., Zhang, j., Wang, Y., Feng, Y., Zhang, X., Sun, X., Li, J., Du, X., Lambert, M. P., Yang, S., Zhao, M., Klein, W. L., Liu, R. (2009) Conformation-dependent single-chain variable fragment antibodies specifically recognize beta-amyloid oligomers, *FEBS Letters* 583, 579-584.

Wirths, O., Bethge, T., Marcello, A., Harmeier, A., Jawhar, S., Lucassen, P. J., Multhaup, G., Brody, D. L., Esparza, T., Ingelsson, M., Kalimo, H., Lannfelt, L., and Bayer, T. A. (2010) Pyroglutamate Abeta pathology in APP/PS1KI mice, sporadic and familial Alzheimer's disease cases, *J. Neural Transm.* 117, 85-96.

Wirths, O., Erck, C., Martens, H., Harmeier, A., Geumann, C., Jawhar, S., Kumar, S., Multhaup, G., Walter, J., Ingelsson, M., Degerman-Gunnarsson, M., Kalimo, H., Huitinga, I., Lannfelt, L., and Bayer, T. A. (2010) Identification of low molecular weight pyroglutamate Abeta oligomers in Alzheimer's disease: a novel tool for therapy and diagnosis, *J. Biol. Chem.* 285, 41517-41524.

Wirths, O., Multhaup, G., and Bayer, T. A. (2004) A modified beta-amyloid hypothesis: intraneuronal accumulation of the beta-amyloid peptide—the first step of a fatal cascade, *J Neurochem* 91, 513-520.

Wittnam, J. L., Portelius, E., Zetterberg, H., Gustaysson, M. K., Schilling, S., Koch, B., Demuth, H.-U., Blennow, K., Wirths, O., and Bayer, T. A. (2012) Pyroglutamate Amyloid β (Aβ) Aggravates Behavioral Deficits in Transgenic Amyloid Mouse Model for Alzheimer's Disease, *Journal of Biological Chemistry* 287, 8154-8162

Youssef I, et al. (2008) N-truncated amyloid-β oligomers induce learning impairment and neuronal apoptosis. *Neurobiol. Aging* 29(9), 1319-1333.

The invention claimed is:

1. A monoclonal antibody recognizing a conformational epitope formed by Phe at amino acid position 4 of trimeric or tetrameric human Aβ,
 as determined by pepscan ELISA comprising the steps of precoating with 100 ng Aβ$_{4-19}$ and Aβ$_{5-20}$, blocking, incubating with 7 µg/ml of said monoclonal antibody, and detecting said monoclonal antibody with a labeled secondary antibody;
 wherein said monoclonal antibody does not bind human monomeric Aβ$_{1-42}$ or human Aβ$_{1-42}$ dimers,
 as determined by native Western-blotting comprising the steps of applying 7 µg Aβ$_{1-42}$ on a 18% SDS-free polyacrylamide gel, transferring on a 0.45 µm nitrocellulose membrane, blocking, incubating with said monoclonal antibody in a concentration of not more than 10 µg/ml for 2 h at room temperature, and detecting said monoclonal antibody with a labeled secondary antibody;
 wherein said monoclonal antibody comprises
 (a) a variable region that comprises a H-CDR1, a H-CDR2 and a H-CDR3 as shown in SEQ ID NOs: 1, 2 and 3, and a L-CDR1, a L-CDR2 and a L-CDR3 as shown in SEQ ID NOs: 4, 5 and 6 (NT4X-83); or
 (b) a variable region that comprises a H-CDR1, a H-CDR2 and a H-CDR3 as shown in SEQ ID NOs: 9, 10 and 11, and a L-CDR1, a L-CDR2 and a L-CDR3 as shown in SEQ ID NOs: 12, 13 and 14 (NT4X-167).

2. The monoclonal antibody of claim 1, wherein the epitope further comprises the amino acids at position 2 and 3 of human Aβ, as determined by pepscan ELISA.

3. The monoclonal antibody of claim 1, wherein the trimeric or tetrameric Aβ oligomers are oligomers of Aβ 1-X, Aβ 4-X, pyro-Glu-Aβ 3-X, or combinations thereof, wherein X is 42, 40 or 38.

4. The monoclonal antibody of claim 3, wherein X is 42.

5. The monoclonal antibody of claim 1, wherein said monoclonal antibody comprises
(a) a variable region comprising an amino acid sequence which is at least 80% identical to the amino acid sequence as shown in SEQ ID NO: 7, and comprising an amino acid sequence which is at least 80% identical to the amino acid sequence as shown in SEQ ID NO: 8 (NT4X-83); or
(b) a variable region comprising an amino acid sequence which is at least 80% identical to the amino acid sequence as shown in SEQ ID NO: 15, and comprising an amino acid sequence which is at least 80% identical to the amino acid sequence as shown in SEQ ID NO: 16 (NT4X-167); or
(c) a variable region comprising an amino acid sequence which is at least 80% identical to the amino acid sequence as shown in SEQ ID NO: 7 (VH NT4X-83); or
(d) a variable region comprising an amino acid sequence which is at least 80% identical to the amino acid sequence as shown in SEQ ID NO: 15 (VH NT4X-167); or
(e) a variable region comprising an amino acid sequence which is at least 80% identical to the amino acid sequence as shown in SEQ ID NO: 8 (VL NT4X-83); or
(f) a variable region comprising an amino acid sequence which is at least 80% identical to the amino acid sequence as shown in SEQ ID NO: 16 (VL NT4X-167).

6. The monoclonal antibody of claim 1, wherein said monoclonal antibody also binds HMW oligomers of Aβ 1-42, pyro-Glu-Aβ 3-42, Aβ 4-42, or combinations thereof, as determined by native Western-blotting comprising the steps of applying 7 μg Aβ$_{1-42}$ on a 18% SDS-free polyacrylamide gel, transferring on a 0.45 μm nitrocellulose membrane, blocking, incubating with said monoclonal antibody in a concentration of not more than 10 μg/ml for 2 h at room temperature, and detecting said monoclonal antibody with a labeled secondary antibody.

7. The monoclonal antibody of claim 1, wherein said monoclonal antibody recognizes aggregates that are specific for Alzheimer's disease, as determined by immunohistochemistry of brain tissue sections.

8. The monoclonal antibody of claim 7, wherein the Alzheimer's disease is familial Alzheimer's disease.

9. The monoclonal antibody of claim 1, wherein said monoclonal antibody inhibits further aggregation of trimeric or tetrameric Aβ oligomers of Aβ 1-X, Aβ 4-X, pyro-Glu-Aβ 3-X, or combinations thereof, wherein X is 42, 40 or 38, when tested in a concentration of 10 μM in 50 mM sodium phosphate buffer, 50 mM NaCl, 20 μM thioflavin T and 0.01% sodium azide, pH 7.4, at 37° C. in a peltier adapter with stirring in a thioflavin T aggregation assay.

10. The monoclonal antibody of claim 9, wherein X is 42.

11. The monoclonal antibody of claim 1, wherein said monoclonal antibody competes for the same epitope with an antibody selected from the group of antibodies consisting of NT4X-83, as deposited under DSM ACC3161, and NT4X-167, as deposited under DSM ACC3162.

12. The monoclonal antibody according to claim 1, wherein said monoclonal antibody is a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a polyvalent antibody-construct, a synthetic antibody, a cross-cloned antibody, a humanized antibody, nanobodies, and diabodies, polyvalent nanobodies or diabodies.

13. The monoclonal antibody according to claim 1, wherein said monoclonal antibody is monoclonal antibody produced by hybridoma as deposited under DSM ACC3161 or hybridoma as deposited under DSM ACC3162.

14. The monoclonal antibody molecule according to claim 1, wherein pepscan ELISA is carried out using a 96 well-plate precoated overnight with 100 ng Aβ$_{4-19}$ and Aβ$_{5-20}$ in 0.05 M carbonate buffer, pH 9.6, at 4° C., which has been subsequently washed three times with 250 μl 0.01 M PBS, blocked with, 200 μl 5% w/v Albumin Fraction V in 0.01 M PBS for 1 h at 25° C., followed by three times washing with 250 μl 0.01 M PBS, and incubating with a concentration of the monoclonal antibody of 7 μg/ml in 100 μl of 5% w/v Albumin Fraction V in 0.01 M PBS for 1 h at 25° C., followed by three times washing with 250 μl 0.01 M PBS, and incubation for 1 h at 25° C. with a horseradish peroxidase conjugated secondary antibody recognizing the monoclonal antibody in 100 μl of 5% w/v Albumin Fraction V in 0.01 M PBS, followed by three times washing with 250 μl 0.01 M PBS, and addition of 50 μl of 3,3',5,5'-Tetramethylbenzidin.

15. The monoclonal antibody according to claim 1, wherein native Western-blotting is carried out using 7 μg Aβ$_{1-42}$ on a 18% SDS-free polyacrylamide gel, semi-dry blotting transfer on a 0.45 μm nitrocellulose membrane, two times washing for 10 min in 1 X TBS/T (0.1 M Tris, 1.5 M NaCl and 0.5% Tween 20) on a rotator with 40 rpm, blocking with 10% non-fat dry milk in 1X TBS/T for 1 h at room temperature on a shaker with 40 rpm, incubation with said monoclonal antibody in a concentration of not more than 10 μg/ml for 2 h at room temperature on a shaker with 40 rpm, two times of washing with 1X TBS/T each for 10 min with 40 rpm shaking, incubation with a secondary antibody conjugated with horseradish peroxidase and recognizing the monoclonal antibody, for 2 h at RT, washing for two times for 10 min with 1X TBS/T, and incubation for 2 min with a solution of 8 ml 0.25 mg/ml luminal in 0.1 M Tris/HCl, comprising 800 μl 1.1 mg/ml paracoumaric acid in DMSO and 2.5 μl H$_2$O$_2$, and exposition to x-ray film.

16. A method of treating Alzheimer's disease, comprising the step of administering a monoclonal antibody according to claim 1 to a subject.

17. The method of claim 16, wherein the Alzheimer's disease is sporadic Alzheimer's disease or familial Alzheimer's disease.

18. A method of diagnosing Alzheimer's disease, comprising the step of detecting the amount of trimeric and tetrameric oligomers of Aβ in a sample of a subject to be diagnosed using a monoclonal antibody according to claim 1.

19. A method of identifying agents useful in the treatment of Alzheimer's disease, comprising the steps of treating a test animal treated with the candidate agent and detecting the amount of trimeric and tetrameric oligomers of Aβ in an immunohistochemistry sample of said animal using a monoclonal antibody according to claim 1.

20. A method of monitoring the efficacy of a treatment of Alzheimer's disease, comprising the step of detecting the amount of trimeric and tetrameric oligomers of Aβ in a sample of a subject to be diagnosed using a monoclonal antibody according to claim 1.

\* \* \* \* \*

UNITED STATES PATENT AND TRADEMARK OFFICE
CERTIFICATE OF CORRECTION

PATENT NO. : 9,617,332 B2
APPLICATION NO. : 14/399639
DATED : April 11, 2017
INVENTOR(S) : Bayer Page 1 of 1

It is certified that error appears in the above-identified patent and that said Letters Patent is hereby corrected as shown below:

In the Specification

Column 23, Lines 15-16, change "NT4X-83 LCDR3 (SEQ ID NO:6): QNDYSYPLTY" to --NT4X-83 LCDR3 (SEQ ID NO:6): QNDYSYPLT--.

Signed and Sealed this
Fourteenth Day of January, 2020

Andrei Iancu
*Director of the United States Patent and Trademark Office*

SEQUENCE LISTING

<160> NUMBER OF SEQ ID NOS: 17

<210> SEQ ID NO 1
<211> LENGTH: 8
<212> TYPE: PRT
<213> ORGANISM: artificial
<220> FEATURE:
<223> OTHER INFORMATION: NT4X-83 HCDR1

```
<400> SEQUENCE: 1

Gly Phe Asn Ile Arg Asp Thr Tyr
1               5

<210> SEQ ID NO 2
<211> LENGTH: 8
<212> TYPE: PRT
<213> ORGANISM: Artificial
<220> FEATURE:
<223> OTHER INFORMATION: NT4X-83 HCDR2

<400> SEQUENCE: 2

Val Asp Pro Ala Asn Gly Asn Thr
1               5

<210> SEQ ID NO 3
<211> LENGTH: 13
<212> TYPE: PRT
<213> ORGANISM: Artificial
<220> FEATURE:
<223> OTHER INFORMATION: NT4X-83 HCDR3

<400> SEQUENCE: 3

Ala Arg Arg Ile Tyr Tyr Gly Tyr Ala Leu Phe Ala Tyr
1               5                   10

<210> SEQ ID NO 4
<211> LENGTH: 12
<212> TYPE: PRT
<213> ORGANISM: Artificial
<220> FEATURE:
<223> OTHER INFORMATION: NT4X-83 LCDR1

<400> SEQUENCE: 4

Gln Ser Leu Leu Asn Ser Gly Asn Gln Lys Asn Tyr
1               5                   10

<210> SEQ ID NO 5
<211> LENGTH: 3
<212> TYPE: PRT
<213> ORGANISM: Artificial
<220> FEATURE:
<223> OTHER INFORMATION: NT4X-83 LCDR2

<400> SEQUENCE: 5

Trp Ala Ser
1

<210> SEQ ID NO 6
<211> LENGTH: 10
<212> TYPE: PRT
<213> ORGANISM: Artificial
<220> FEATURE:
<223> OTHER INFORMATION: NT4X-83 LCDR3

<400> SEQUENCE: 6

Gln Asn Asp Tyr Ser Tyr Pro Leu Thr Tyr
1               5                   10

<210> SEQ ID NO 7
<211> LENGTH: 120
<212> TYPE: PRT
<213> ORGANISM: Artificial
<220> FEATURE:
<223> OTHER INFORMATION: NT4X-83 VH
```

-continued

```
<400> SEQUENCE: 7

Glu Val His Leu Gln Gln Ser Gly Ala Glu Leu Val Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Lys Gln Arg Pro Glu Gln Gly Leu Glu Trp Ile
        35                  40                  45

Gly Arg Val Asp Pro Ala Asn Gly Asn Thr Lys Tyr Asp Pro Lys Phe
    50                  55                  60

Gln Gly Lys Ala Thr Ile Thr Ala Asp Thr Ser Ser Asp Thr Ala Tyr
65                  70                  75                  80

Leu Gln Leu Ser Ser Leu Thr Ala Glu Asp Thr Ala Val Tyr Phe Cys
                85                  90                  95

Ala Arg Arg Ile Tyr Tyr Gly Tyr Ala Leu Phe Ala Tyr Trp Gly Gln
            100                 105                 110

Gly Thr Leu Val Thr Val Ser Ala
        115                 120

<210> SEQ ID NO 8
<211> LENGTH: 113
<212> TYPE: PRT
<213> ORGANISM: Artificial
<220> FEATURE:
<223> OTHER INFORMATION: NT4X-83 VL

<400> SEQUENCE: 8

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 9
<211> LENGTH: 8
<212> TYPE: PRT
<213> ORGANISM: Artificial
<220> FEATURE:
<223> OTHER INFORMATION: NT4X-167 HCDR1

<400> SEQUENCE: 9

Gly Phe Ser Leu Thr Ser Tyr Gly
1               5

<210> SEQ ID NO 10
<211> LENGTH: 7
<212> TYPE: PRT
<213> ORGANISM: Artificial
<220> FEATURE:
<223> OTHER INFORMATION: NT4X-167 HCDR2
```

<400> SEQUENCE: 10

Met Trp Ser Gly Gly Ile Thr
1               5

<210> SEQ ID NO 11
<211> LENGTH: 10
<212> TYPE: PRT
<213> ORGANISM: Artificial
<220> FEATURE:
<223> OTHER INFORMATION: NT4X-167 HCDR3

<400> SEQUENCE: 11

Ala Arg Gly Ser Arg Tyr Ala Leu Asp Tyr
1               5                   10

<210> SEQ ID NO 12
<211> LENGTH: 6
<212> TYPE: PRT
<213> ORGANISM: Artificial
<220> FEATURE:
<223> OTHER INFORMATION: NT4X-167 LCDR1

<400> SEQUENCE: 12

Gln Asp Ile Ser Asn Tyr
1               5

<210> SEQ ID NO 13
<211> LENGTH: 3
<212> TYPE: PRT
<213> ORGANISM: Artificial
<220> FEATURE:
<223> OTHER INFORMATION: NT4X-167 LCDR2

<400> SEQUENCE: 13

Tyr Thr Ser
1

<210> SEQ ID NO 14
<211> LENGTH: 9
<212> TYPE: PRT
<213> ORGANISM: Artificial
<220> FEATURE:
<223> OTHER INFORMATION: NT4X-167 LCDR3

<400> SEQUENCE: 14

Gln Gln Gly Asn Thr Leu Pro Pro Thr
1               5

<210> SEQ ID NO 15
<211> LENGTH: 116
<212> TYPE: PRT
<213> ORGANISM: Artificial
<220> FEATURE:
<223> OTHER INFORMATION: NT4X-167 VH

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Ile His Trp Val Arg Gln Ser Pro Gly Lys Gly Leu Glu Trp Leu
            35                  40                  45

Gly Val Met Trp Ser Gly Gly Ile Thr Asp Phe Tyr Ala Ala Phe Ile
        50                  55                  60

```
Ser Arg Leu Ser Ile Ser Arg Asp Ile Ser Lys Ser Gln Val Phe Phe
 65              70                  75                  80

Lys Met Asn Ser Leu Gln Ala Asp Asp Thr Ala Ile Tyr Tyr Cys Ala
                 85                  90                  95

Arg Gly Ser Arg Tyr Ala Leu Asp Tyr Trp Gly Gln Gly Thr Ser Val
                100                 105                 110

Ser Val Ser Ser
        115

<210> SEQ ID NO 16
<211> LENGTH: 107
<212> TYPE: PRT
<213> ORGANISM: Artificial
<220> FEATURE:
<223> OTHER INFORMATION: NT4X-167 VL

<400> SEQUENCE: 16

Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Pro
                 85                  90                  95

Thr Phe Gly Gly Gly Thr Lys Leu Glu Ile Lys
                100                 105

<210> SEQ ID NO 17
<211> LENGTH: 42
<212> TYPE: PRT
<213> ORGANISM: Homo sapiens

<400> SEQUENCE: 17

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
                 20                  25                  30

Gly Leu Met Val Gly Gly Val Val Ile Ala
                 35                  40
```